United States Patent [19]
Zenke et al.

[11] Patent Number: 5,648,248
[45] Date of Patent: Jul. 15, 1997

[54] METHODS FOR PRODUCING DIFFERENTIATED CELLS FROM IMMATURE HEMATOPOIETIC CELLS

[75] Inventors: Martin Zenke, Schönow, Germany; Guido Boehmelt, North York, Canada; Jaime Madruga, Berlin, Germany; Paula Enrietto, Stony Brook, N.Y.

[73] Assignee: Boehringer Ingelheim International GmbH, Germany

[21] Appl. No.: 377,731

[22] Filed: Jan. 25, 1995

Related U.S. Application Data

[63] Continuation-in-part of Ser. No. 366,797, Dec. 30, 1994, abandoned.
[51] Int. Cl.$^6$ .................................................. C12N 15/64
[52] U.S. Cl. ................................. 435/172.3; 435/377
[58] Field of Search .......................... 435/172.1, 172.3, 435/240.2, 320.1

[56] References Cited

FOREIGN PATENT DOCUMENTS

| | | |
|---|---|---|
| 0 235 113 | 9/1987 | European Pat. Off. |
| WO93/18137 | 9/1993 | WIPO |
| WO93/20185 | 10/1993 | WIPO |
| WO93/20186 | 10/1993 | WIPO |
| WO94/28113 | 12/1994 | WIPO |

OTHER PUBLICATIONS

Ballard et al., "The v-rel Oncogene Encodes a κB Enhancer Binding Protein That Inhibits NF-κB Function," *Cell* 63:803-814 (1990).
Barth et al., "Reticuloendotheliosis Virus REV-T (REV-A)-Induced Neoplasia: Development of Tumors within the T-Lymphoid and Myeloid Lineages," *J. Virol.* 64(12) : 6054-6062 (1990).
Beug, H. and Graf, T., "Co-operation between viral oncogenes in avian erythroid and myeloid leukaemia," *Eur. J. Clin. Invest.* 19:491-502 (1989).
Beug et al., "Hematopoietic Cells Transformed in Vitro by REV$_T$ Avian Reticuloendotheliosis Virus Express Characteristics of Very Immature Lymphoid Cells," *Virology* 115:295-309 (1981).
Boehmelt et al., "Hormone-regulated v-rel estrogen receptor fusion protein: reversible induction of cell transformation and cellular gene expression," *EMBO J.* 11(12):4641-4652 (1992).
Bose, Jr., H.R., "The Rel family: models for transcriptional regulation and oncogenic transformation," *Chimica et Biophysica Acta* 1114:1-17 (1992).
Bowler et al., "Novel Steroidal Pure Antiestrogens," *Steroids* 54(1) :71-99 (1989).
Burk, O. and Klempnauer, K.H., "Estrogen-dependent alterations in differentiation state of myeloid cells caused by a v-myb/estrogen receptor fusion protein," *EMBO J.* 10(12) :3713-3719 (1991).
Capobianco, A.J., and Gilmore, T.D., "A Conditional Mutant of vRel Containing Sequences from the Human Estrogen Receptor," *Virology* 193:160-170 (1993).

Eilers et al., "Chimaeras of Myc oncoprotein and steroid receptors cause hormone-dependent transformation of cells," *Nature* 340:66-68 (1989).
Gilmore, T.D., "Malignant transformation by mutant Rel proteins," *TiG* 7(10) : 318-322 (1991).
Inaba et al., "Generation of Large Numbers of Dendritic Cells from Mouse Bone Marrow Cultires Supplemented with Granulocyte/Macrophage Colony-stimulating Factor," *J. Exp. Med.* 176:1693-1702 (1992).
Inaba et al., "Granulocytes, macrophages, and dendritic cells arise from a common major histocompatibility complex class II-negative progenitor in mouse bone marrow," *PNAS USA* 90:3038-3042 (1993).
Jackson et al., "Hormone-conditional transformation by fusion proteins of c-Abl, and its transforming variants" *EMBO J.* 12(7) :2809-2819 (1993).
Louvion et al., "Fusion of GAL4-VP16 to a steroid-binding domain provides a tool for gratuitous induction of galactose-responsive genes in yeast," *Gene* 131:129-134 (1993).
Paglia et al., "Immortalized Dendritic Cell Line Fully Competent in Antigen Presentation Primary T Cell Responses In Vivo," *J. Exp. Med.* 178:1893-1901 (1993).
Picard et al., "A Movable and Regulable Inactivation Function within the Steroid Binding Domain of the Glucocorticoid Receptor," *Cell* 54:1073-1080 (1988).
Radke et al., "Transformation of Both Erythroid and Myeloid Cells by E26, an Avian Leukemia Virus That Contains The myb Gene," *Cell* 31:643-653 (1982).
Romani et al., "Proliferating Dendritic Cell Progenitors in Human Blood," *J. Exp. Med.* 180:83-93 (1994).
Sallusto, F. and Lanzavecchia, A., "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α, " *J. Exp. Med.* 179:1109-1118 (1994).

(List continued on next page.)

*Primary Examiner*—James Ketter
*Attorney, Agent, or Firm*—Sterne, Kessler, Goldstein & Fox p.l.l.c.

[57] ABSTRACT

The present invention concerns methods for producing differentiated cells from immature hematopoietic cells. Preferably, a gene coding for a conditional v-rel estrogen receptor fusion protein, v-relER, that causes estrogen-dependent but otherwise unaltered v-rel-specific transformation, is introduced into bone marrow cells. Following inactivation of v-relER oncoprotein activity by administration of an estrogen antagonist, cells differentiate into antigen-presenting dendritic cells as judged by several morphological and functional criteria. Additionally, under different culture conditions, v-relER cells differentiate into cells resembling polymorphonuclear neutrophils. The invention further concerns differentiated cells obtained by the claimed method as well as their use for screening of potentially immunomodulatory substances and in the development of vaccines.

28 Claims, 17 Drawing Sheets

OTHER PUBLICATIONS

Scherrer et al., "Evidence that the Hormone Binding Domain of Steroid Receptors Confers Hormonal Control on Chimeric Proteins by Determining Their Hormone–Regulated Binding to Heat–Shock Protein 90," *Biochemistry* 32:5381–5386 (1993).

Superti–Furga et al., "Hormone–dependent transcriptional regulation and cellular transformation by Fos–steroid receptor fusion proteins," *PNAS USA* 88:5114–5118 (1991).

Umek et al., "CCAAT–Enhancer Binding Proteins: A Component of a Differentiation Switch," *Science* 251:288–292 (1991).

White, D.W. and Gilmore, T.D., "Temperature–Sensitive Transforming Mutants of the v–rel Oncogene," *J. Virology* 67:6876–6881 (1993).

Zenke et al., "v–erbA Specifically Suppresses Transcription of the Avian Erythrocyte Anion Transporter (Band 3) Gene," *Cell* 52:107–119 (1988).

Zhang et al., "The v–rel Oncogene of Avian Reticuloendotheliosis Virus Transforms Immature and Mature Lymphoid Cells of the B Cell Lineage in Vitro," *Virology* 183:457–466 (1991).

Boehmelt, G., et al., "A hormone–inducible v–rel estrogen receptor fusion as a means to transform early hematopoietic progenitor cells and to study their differentiation pathway," *Avian Immunol. Prog.* 62:337–341 (Aug.–Sep. 1993).

Boehmelt, G., et al., "Dendritic Cell Progenitor Is Transformed by a Conditional v–Rel Estrogen Receptor Fusion Protein v–ReLER," *Cell* 80:341–352 (Jan. 27, 1995).

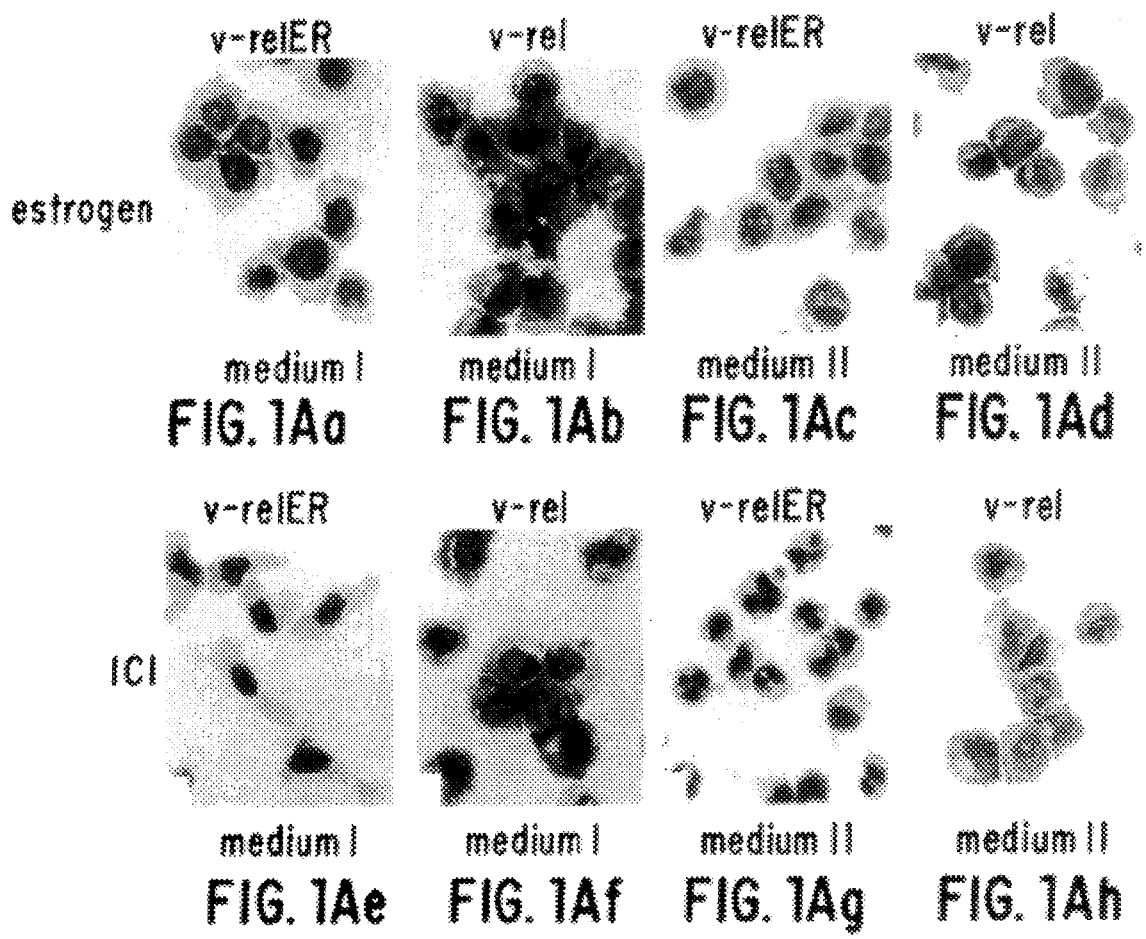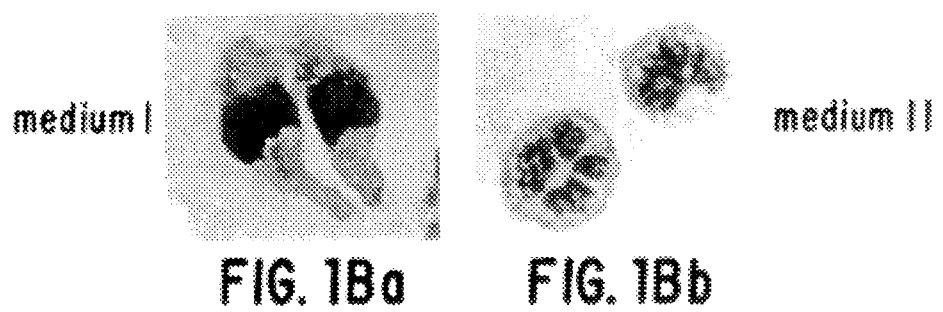

METHODS FOR PRODUCING DIFFERENTIATED CELLS FROM IMMATURE HEMATOPOIETIC CELLS

CROSS REFERENCE TO RELATED APPLICATIONS

This application is a continuation-in-part of application Ser. No. 08/366,797, filed Dec. 30, 1994, which is herein incorporated by reference.

BACKGROUND OF THE INVENTION

1. Field of the Invention

The present invention relates to methods for producing substantially homogenous cell populations of functionally differentiated cells, preferably antigen-presenting dendritic cells or polymorphonuclear neutrophils, from hematopoietic cells.

2. Technical Background

Differentiation of hematopoietic cells involves the highly ordered and controlled proliferation of immature progenitor cells and their commitment and differentiation into fully mature cells of various lineages. While a number of retroviral oncogenes efficiently bypass such normal control mechanisms and cause leukemia, they also provide invaluable tools to study mechanisms of normal hematopoietic cell differentiation on the molecular level. In the avian system, oncogene transformed, non established cell strains can be obtained in vitro under conditions where they retain their capacity to undergo apparently normal terminal differentiation (reviewed in Beug and Graf, 1989).

v-rel, the oncogenic version of c-rel transduced by the avian retrovirus REV-T/REV-A, belongs to the NF-κB/rel/ dorsal transcription factor family (reviewed by Gilmore, 1991). Members of this still growing protein family are versatile regulators involved in growth control, differentiation and pattern formation. v-rel encodes a 59 kd protein which forms multiple complexes with several other cellular proteins (Morrison et al., 1989; 1992; Gilmore, 1991 and references therein) and transforms avian hematopoietic cells both in vivo and in vitro (reviewed in Bose, 1992).

Several groups have demonstrated that v-rel acts as a transcriptional repressor of rel- and/or NF-kB-responsive genes in transient transfection assays (Ballard et al., 1990; Inoue et al., 1991; Richardson and Gilmore, 1991; McDonnell et al., 1992; Ballard et al., 1992). Studies with a conditional hormone-inducible v-rel/estrogen receptor fusion protein (v-relER), however, provided first clues as of v-rel acting as a transcriptional activator of rel- and/or NF-κB-responsive genes in transformed bone marrow cells (Boehmelt et at., 1992). Such a hormone-inducible v-relER caused estrogen-dependent but otherwise unaltered v-rel-specific transformation of chicken bone marrow cells in vitro.

Initial evidence suggested that v-rel contained within the REV-T/REV-A virus complex induced a disease of lymphomatous origin (Sevoian et al., 1964). This is in line with the observation that oncogenic activation of other members of the NF-κB/rel/dorsal family (e.g., Lyt-10/NF-κB2) has been implicated in lymphoid tumor formation in humans (Neri et al., 1991; Lu et al., 1991; Fracchiolla et al., 1993). The in vitro target cell for v-rel transformation was also classified as lymphoid, more specifically, as early preB- or preB/preT-lymphoid progenitor (Beug et al., 1981; Lewis et al., 1981). Finally, REV-T transformation carried out with helper viruses other than REV-A appeared to be of B-lymphoid origin (Barth and Humphries, 1988; Benatar et al., 1991, 1992; Bose, 1992).

Histological studies, however, suggested that the REV-T/ REV-A-induced disease was reticuloendotheliosis (Theilen et al., 1966; Olson, 1967) rather than lymphomatosis, since cells of the reticuloendothelial system (RES) were affected. RES is a collective term for a system of scattered phagocytic cells associated with endothelia of blood vessels and with sinusoids of spleen, liver and lymphoid organs. Cells of the RES are also dispersed in the connective tissue surrounding endothelia and were described to exhibit a high degree of flexibility and mobility.

However, there are few studies in line with these histological characterizations. Barth et al. (1990) showed that the tissue derived from liver or spleen tumors of REV-T/REV-A infected chickens yields transformed cells exhibiting either T-lymphoid or myeloid determinants as demonstrated by surface antigen expression. Using a replication competent virus containing v-rel, Morrison et al. (1991) demonstrated that v-rel transformed chicken bone marrow cells coexpress surface antigens specific to both lymphoid and myeloid cells. Thus, the true target cell for v-rel transformation remained obscure.

Coexpression of lineage-specific cell surface markers is often observed on human leukemic cells, probably due to aberrant gene expression associated with the leukemic phenotype (McCulloch, 1983; Greaves et at., 1986 and references therein). By analogy, coexpression of both myeloid- and lymphoid-specific surface antigens on v-rel transformed cells could be the result of aberrant gene expression induced by the active v-rel oncogene. Alternatively, as suggested before, v-rel transformed cells might represent early, potentially bi- or pluripotent hematopoietic progenitors with the capacity to differentiate into two (or more) mature cell types (Morrison et al., 1991; Boehmelt et al., 1992).

Dendritic cells are found at various locations within an organism and have been classified as e.g., dendritic/ Langerhans cells in the skin, "veiled" cells, interdigitating cells, or follicular dendritic cells, depending on their presumptive function and location (Steinman et al., 1991). They are considered to capture antigens and migrate to lymphoid organs where they present the processed antigens to lymphoid cells. While it is well established that they represent professional antigen-presenting cells, it is still a matter of debate how the different types of dendritic cells relate to each other.

Dendritic cells have been obtained from peripheral blood, bone marrow, spleen (Inaba et al., 1992, 1993) and by in vitro differentiation from CD34+ human peripheral blood stem cells (Caux et al., 1992). A detailed analysis of their functional and biochemical properties has remained difficult, mainly because pure and homogenous cell populations are not yet available and because of the limited cell numbers obtained. Very recently, a v-myc transformed immortalized mouse cell line with features of dendritic cells (or of a late dendritic cell progenitor) was described (Paglia et al., 1993) which should facilitate the analysis of mouse dendritic cells in vitro. Additionally, specific culture conditions were developed for propagation of human dendritic cells, which, however, rapidly slowed down in growth after 3 weeks in culture (Romani et al., 1994; Sallusto a Lanzavecchia, 1994).

To achieve a better understanding of molecular mechanisms of disease and for the search of new drugs, there is a need for in vitro models of vertebrate cell systems, especially culture systems, containing well-defined, homogenous populations of differentiated cells which exhibit all or all essential parts of their normal physiological function. Transformation of immature hematopoietic cells with a regulatable oncogene product, a conditionally active v-rel (e.g., v-relER; Boehmelt et al., 1992; Capobianco and Gilmore, 1993) has opened the possibility of reversibly inducing growth of bone marrow cells and concomitantly blocking their differentiation. However, while such cells can be expanded in vitro under specific culture conditions, methods for inducing cellular differentiation have not appeared in the literature.

SUMMARY OF THE INVENTION

The invention provides methods for inducing differentiation of transformed hematopoietic cells during culture. The method involves: introducing into the hematopoietic cells an oncogene capable of expressing an oncoprotein, wherein the oncoprotein is capable of transforming immature hematopoietic cells; culturing the cells in a first culture medium under conditions wherein the oncogene expresses the oncoprotein which promotes cellular growth while at least partially inhibiting cellular differentiation; deactivating the oncoprotein or expression from the oncogene; and culturing the cells in a second culture medium capable of supporting growth of differentiated hematopoietic cells.

In one aspect, the present invention provides methods for producing differentiated cells from immature hematopoietic cells, said differentiated cells having morphological and functional characteristics of antigen-presenting dendritic cells. Preferably, the dendritic cells are highly mobile, fully differentiated antigen-presenting dendritic cells.

In another aspect, the methods of the invention provides methods for producing differentiated cells from immature hematopoietic cells, said differentiated cells having morphological and functional characteristics of polymorphonuclear neutrophils.

In a preferred embodiment, an oncogene encoding the hormone-dependent variant v-rel/ER fusion protein is used to transform the hematopoietic cells during culture in a first culture medium in the presence of estrogen. The first culture medium can be any culture medium known in the art as suitable for culturing transformed bone marrow cells and which is compatible with the conditions necessary for oncogene regulation.

During or after culture in the first culture medium, deactivation of oncoprotein activity may be performed according to any suitable technique. These include the use of anti-sense nucleic acid constructs complementary to the oncogene, monoclonal antibodies specific for the oncoprotein, raising the temperature to non-permissive levels if the oncogene encodes a temperature sensitive mutant, and adding a hormone antagonist or simply removing the hormone if the oncoprotein is a hormone-dependent fusion protein comprising an oncoprotein fused to a hormone receptor. If the hormone-dependent fusion protein is v-rel/ER, then the antagonist is preferably ICI 164,384 (ICI).

The second culture medium should fit the needs of the type of the differentiated cells to be produced. For production of dendritic cells, a second culture medium containing transferrin (e.g., chicken conalbumin) and/or insulin is preferred. To obtain highly mobile antigen-presenting dendritic cells, this medium should be supplemented with fibroblast conditioned medium. A second culture medium based essentially on CFU-E medium is well-suited for the production of cells having properties of polymorphonuclear neutrophils.

By the invention, oncogenes can be introduced into the hematopoietic cells according to any suitable technique. These include, but are not limited to, electroporation, injection of "naked" or liposomally-encapsulated DNA, and transduction with packaged virions. Preferably, the oncogene is introduced into the hematopoietic cells by viral infection.

BRIEF DESCRIPTION OF THE FIGURES

FIG. 1: Morphology of differentiated v-relER cells. (A) v-relER and v-rel cells (clones 25 and C8, respectively) were cultured in standard growth medium (a,b), in medium I (e,f) and in medium II (c,d,g,h) in the presence of estrogen or ICI as indicated. After three days cells were cytocentrifuged onto slides and stained according to May-Grünwald/Giemsa. The characteristic morphological changes shown here for v-relER clone 25 were also observed for other v-relER cell clones when cultured under identical conditions. (B) Medium I and II differentiated v-relER cells at higher magnification. Please note the characteristic polarized appearance of elongated v-relER cells differentiated in medium I (a) and the segmented, multilobed nucleus characteristic for v-relER cells differentiated in medium II (b).

Figure 2A:
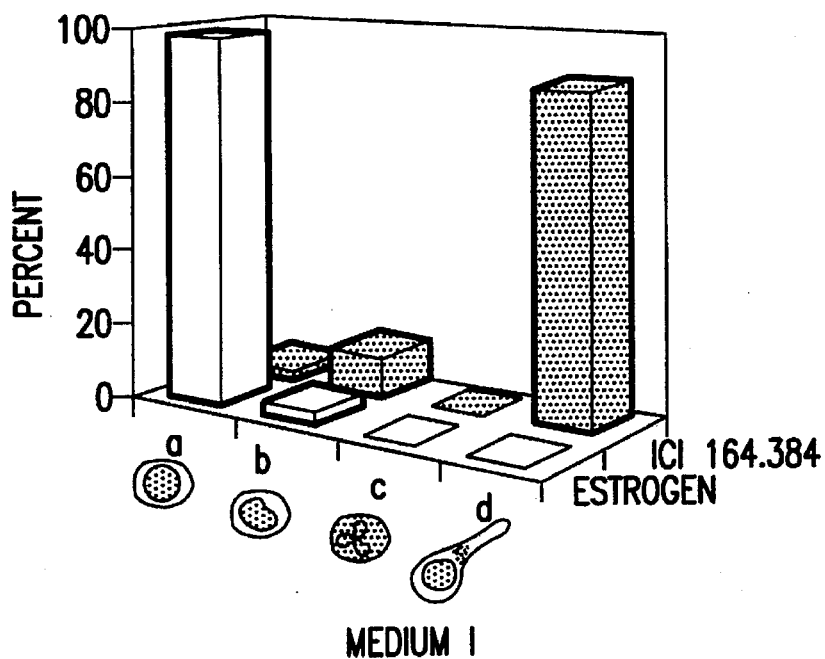
FIG. 2: Relative proportion of differentiated v-relER cells obtained in medium I and II. v-relER cells (clone 23) were differentiated in medium I and II (A and B, respectively). After 3 and 4 days (A and B, respectively) aliquots were cytocentrifuged onto slides and stained according to May-Grünwald/Giemsa. The relative proportion of four characteristic morphological phenotypes was determined by evaluating 400 to 900 cells under brightfield illumination. Phenotypes a and b represent undifferentiated, blast-like cells containing a rounded or kidney-shaped nucleus, respectively. Cells with a polymorph nucleus are depicted as phenotype c; elongated cells with a polarized appearance are represented by phenotype d. The differentiation pattern obtained for v-relER cell clone 23 is representative for virtually all v-relER clones studied.

B) V-relER cells incubated in CCE-medium for 2 days in the presence of ICI are highly motile as revealed by time-lapse photography. Cells migrate on the surface of the tissue culture dish about 4–5 times their bodylength within 10 minutes (arrow points to one representative cell). Cells allowed to adhere in the presence of estrogen do not migrate (not shown).

C) Time-lapse cinemicroscopy using normal spleen-derived dendritic cells. Please note that the characteristic way of movement and the high mobility of spleen derived "veiled" dendritic cells is very reminiscent to the movement of dendritic v-relER cells.

FIG. 7: Maturation of neutrophils upon v-relER inactivation in medium II. A) Maturation of v-relER cells into neutrophils reveals several intermediate stages. Shown are immature cells with a round nucleus (stage 1), cells with a notched or horseshoe-shaped nucleus (stage 2), stage 3 cells with a indented nucleus and cells with a segmented multi-lobed nucleus (stage 4).

B) Time course of differentiation into polymorphonuclear leukocytes. Cytospin preparations of v-relER cells induced to differentiate in medium II were used to evaluate the proportion of differentiation stages as depicted in (A).

C) Freshly isolated chicken bone marrow contains neutrophils similar to differentiation stages 3 or 4.

D) Periodic acid Schiff (PAS) staining reveals a coarse pattern in v-relER neutrophils differentiated in medium II and ICI (ICI), whereas estrogen-treated (estrogen) or dendritic v-relER cells (not shown) are negative.

May-Grünwald/Giemsa and PAS staining shown in (A) and (B) were photographed using the same magnification. Cells stained with PAS-reagent in (D) are shown with a lower magnification. The results in (A) and (C) were obtained using v-relER clone 23; cells depicted in panel (D) are from v-relER clone 25.

Figure 8A:
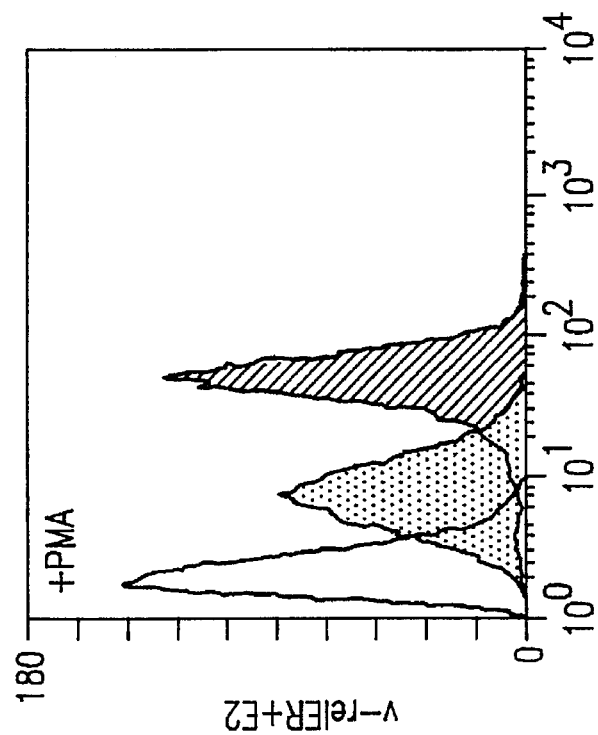
Figure 8A:
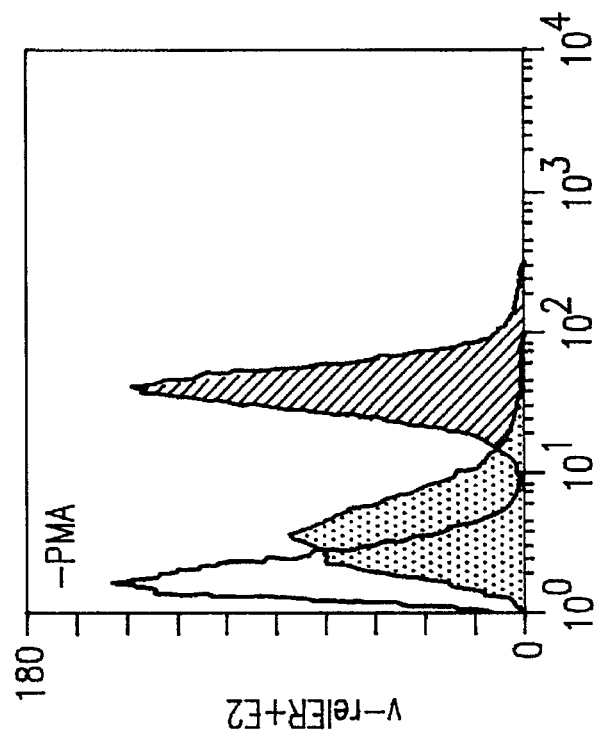
Figure 8A:
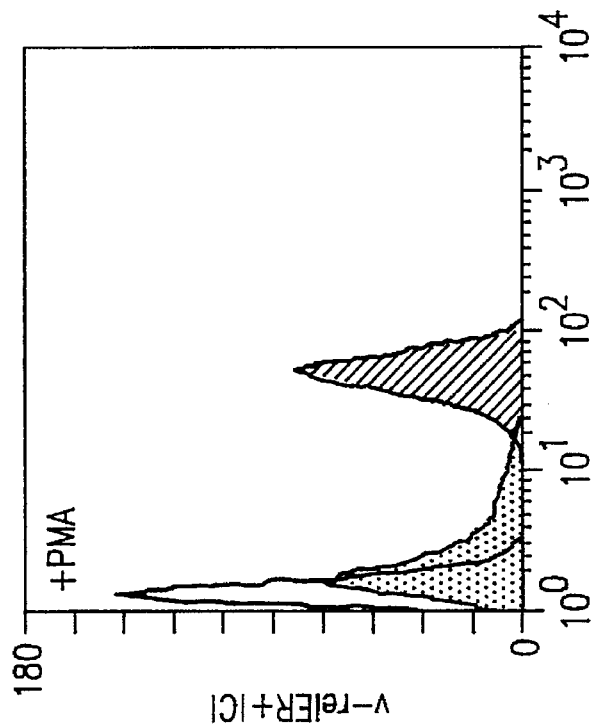
Figure 8A:
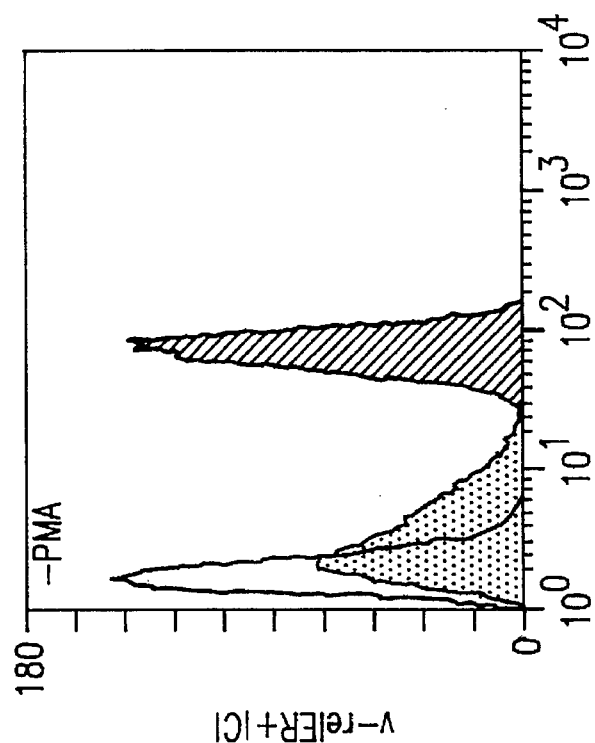
Figure 8A:
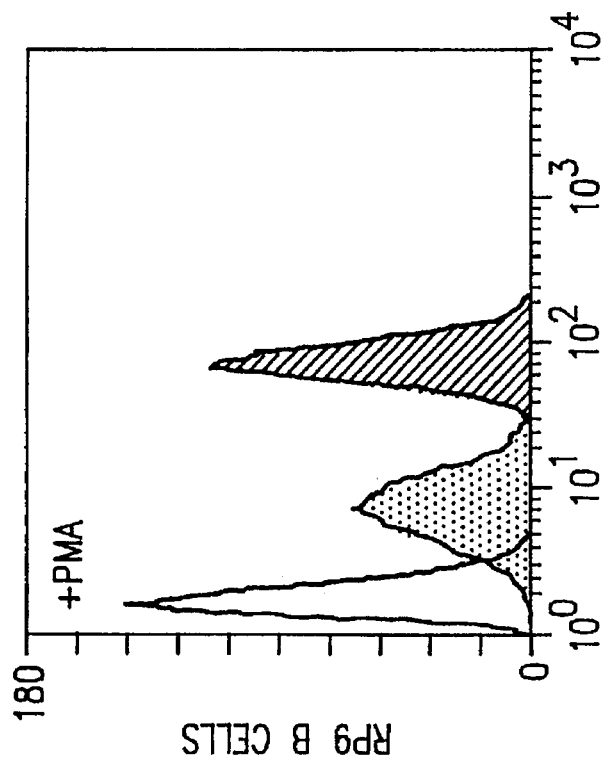
Figure 8A:
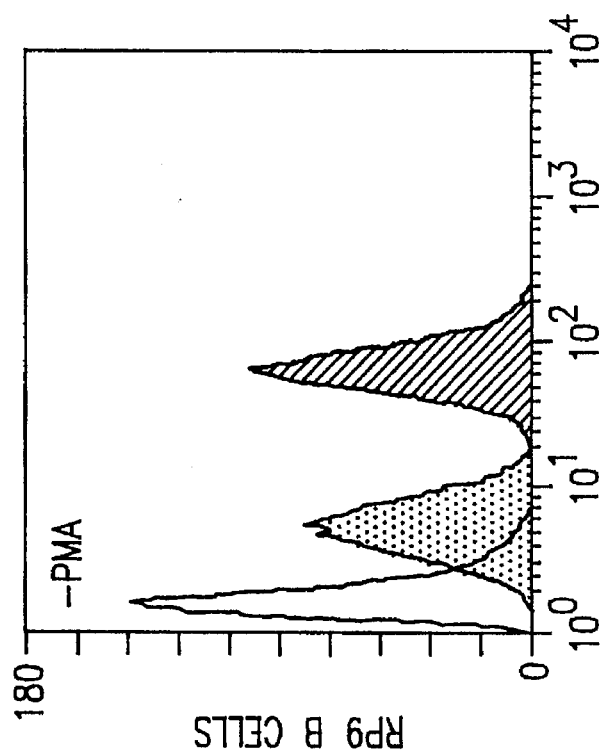
Figure 8A:
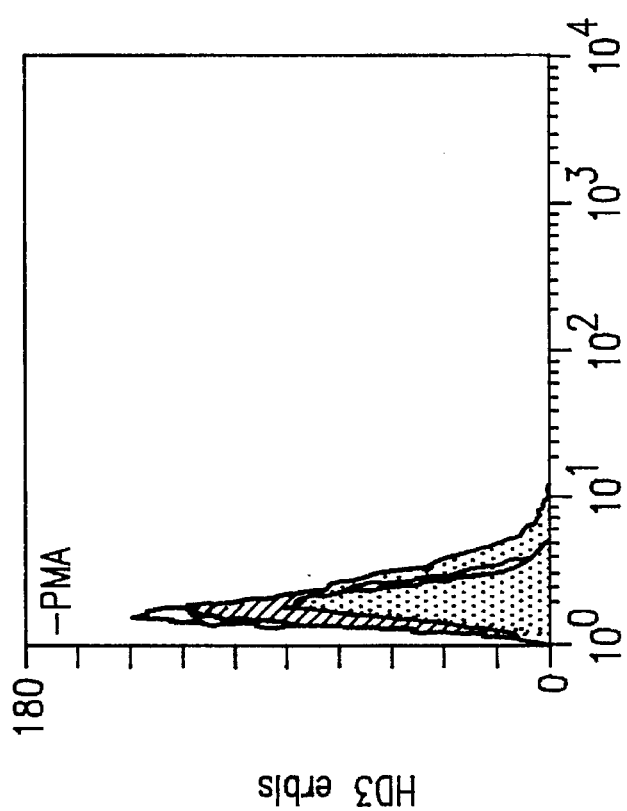
Figure 8A:
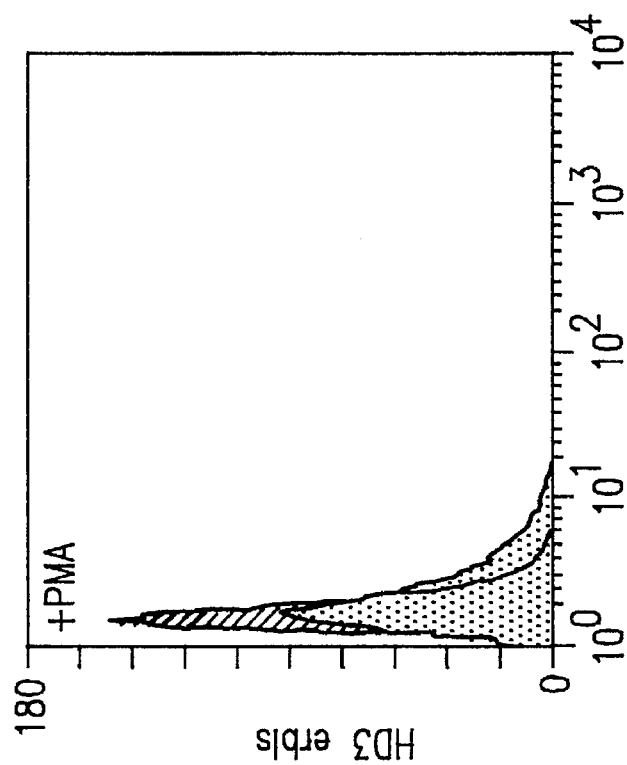
Figure 8B:
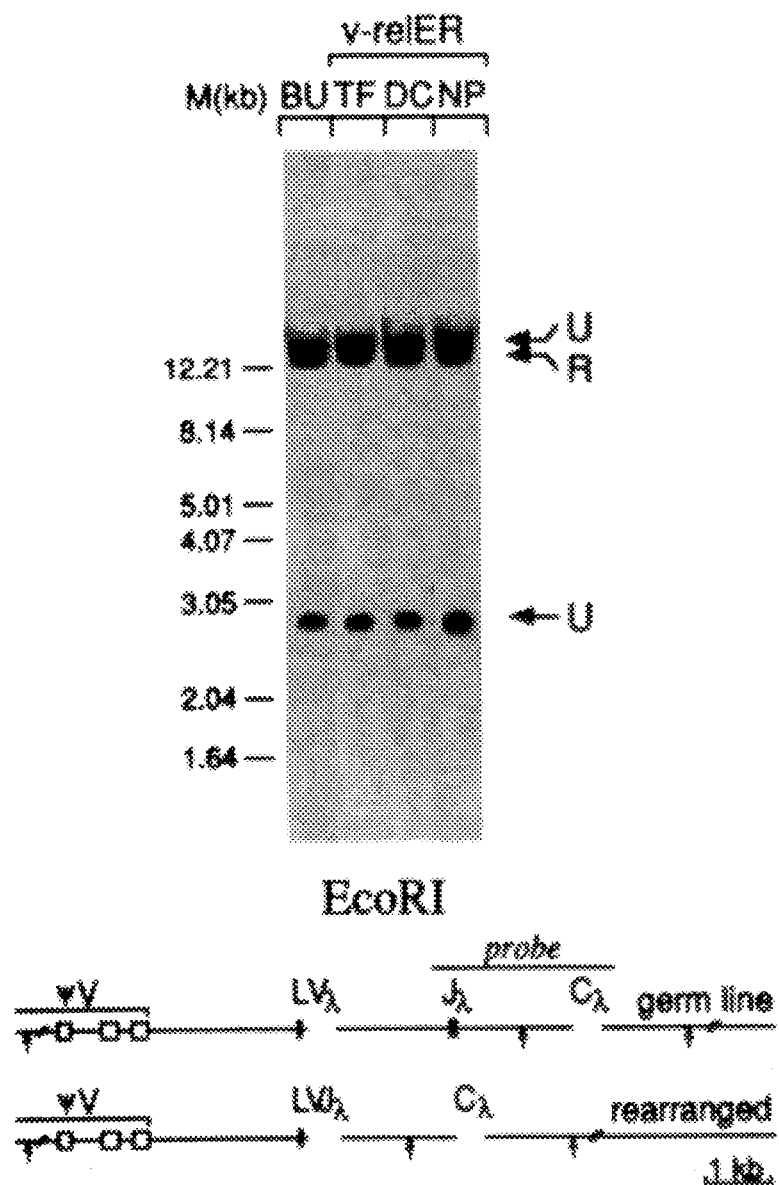

FIGS. 8A and 8B: B-lymphoid determinants of transformed v-relER cells. A) V-relER cells express surface IgM. FACS analysis using monoclonal antibodies specific for the constant region of the chicken Cµ heavy chain (gray) or the nonpolymorph region of chicken B-L (MHC class II) β-chain (hatched). Antigen/antibody complexes on the cellular surface were detected using a FITC-conjugated goat-anti-mouse IgG. Controls were incubated with FITC-labeled secondary antibody (white). V-relER cells were cultured under various conditions: for three days in standard growth medium plus estrogen (a), in medium I plus ICI (c) or in a medium containing phorbol 12-myristate 13-acetate (PMA, Experimental Procedures) supplemented with estrogen or ICI, respectively (b, d). Cells of a chicken B cell line (RP9; e, f) or cells of a chicken erythroid cell line (HD3 erbls; g, h) were incubated in standard growth medium in the absence (e, g) or presence (f, h) of PMA as indicated.

B) Rearrangement of the immunoglobulin light chain gene (Igλ) in v-relER cells. Southern blot of genomic DNA isolated from chicken bursa (BU), transformed (TF), dendritic (DC) and neutrophil (NP) v-relER cells following digestion with EcoRI. The probe used was a BamHI/SalI fragment spanning the $J_\lambda$–$C_\lambda$ region as depicted in the scheme below. DNA fragments derived from the rearranged (R) or germline (U) alleles are indicated. Numbers refer to the relative size (kb) according to DNA marker (M). The scheme shown compares the germ line to the rearranged configuration of the chicken Igλ gene (Reynaud et al., 1987). ψV cluster of pseudogenes, L leader sequence, $V_\lambda$ variable region, $J_\lambda$ joining segment, $C_\lambda$ constant region, arrows indicate EcoRI restriction sites.

Figure 9A:
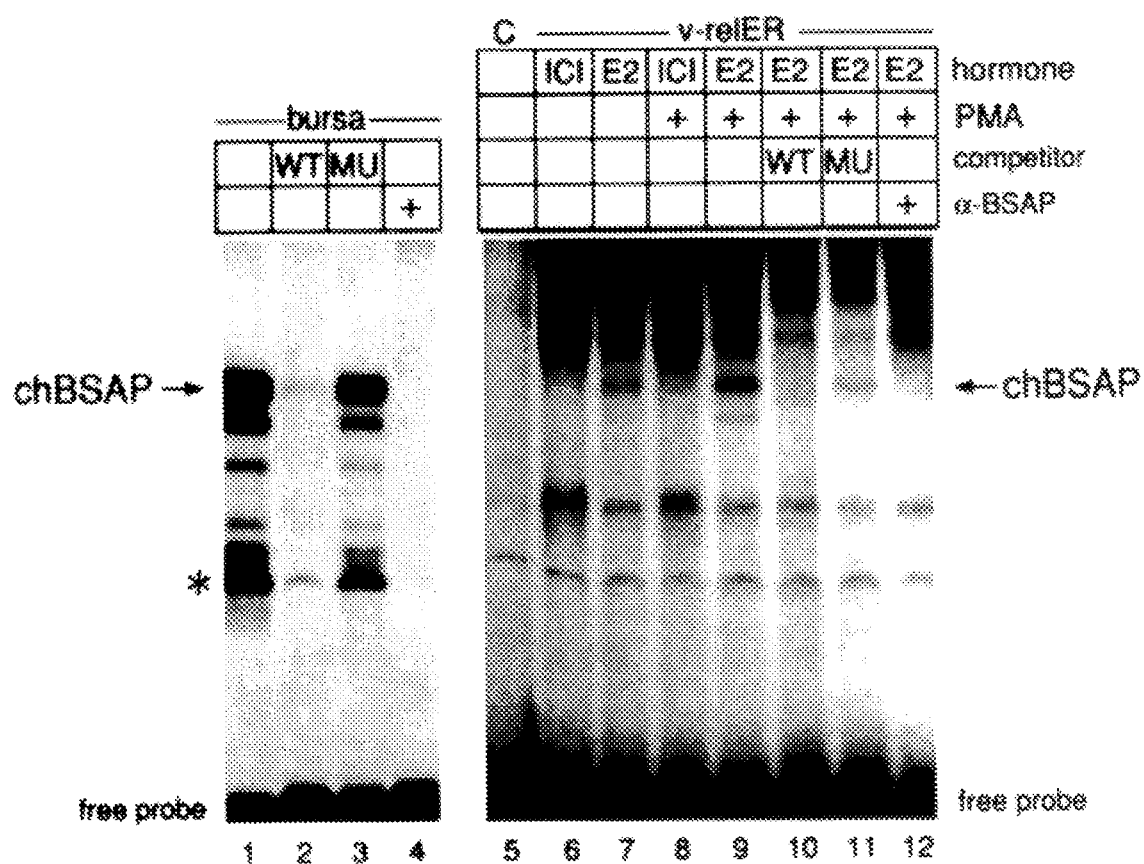
Figure 9B:
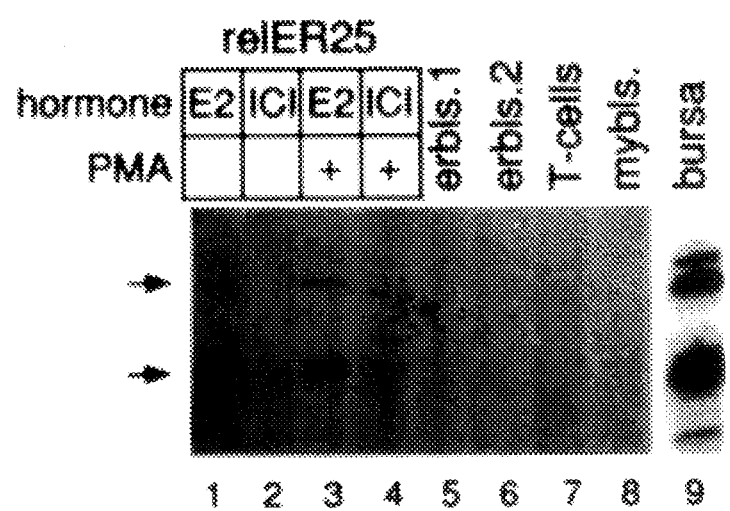

FIGS. 9A and 9B: BSAP expression in v-relER cells. A) Modulation of BSAP expression in v-relER cells. Nuclear extracts from v-relER cells (v-relER) grown under conditions as indicated in FIG. 8, bursa cells (bursa) and control CEFs (C) were subjected to electrophoretic mobility shift assay (EMSA) using an oligonucleotide with a murine BSAP binding site. The chicken BSAP-specific band (chBSAP) is indicated. WT and MU refer to wildtype and mutant oligonucleotide used as competitor. A murine BSAP-specific antibody (αBSAP) interferes with DNA binding (lanes 4, 12). Please note that chicken BSAP activity can be enhanced by PMA-treatment in the presence of estrogen (compare lanes 7 and 9), whereas differentiation induction by ICI leads to a loss of chBSAP activity in v-relER cells (compare lanes 6, 7 and lanes 8, 9). * indicates a BSAP-specific degradation product. The autoradiograms in the left or right panel were exposed for 8 or 48 hours, respectively.

B) chBSAP mRNA expression. Total RNA (10 µg) was analysed by RNAse protection using a probe specific for the paired domain of chBSAP. V-relER cells (clone 25) were grown under conditions as described in FIG. 8 (lanes 1–4). chBSAP expression was analysed in HD3 (tsv-erbB+v-erbA transformed) erythroblasts (erbls. 1), in normal erythroid progenitors grown in the presence of SCF, TGFα and estrogen (erbls.2), in MSB-1 T cells (T cells), in HD11 (MC29 v-myc transformed) macrophages (mybls.) and in chicken bursa (bursa). The specific protected fragments are indicated (arrows). The two smaller fragments observed are due to artificial restriction enzyme recognition sequences in the PCR primers used to clone chBSAP cDNA. The autoradiogram shown for lanes 1–8 and lane 9 are exposed for 7 days and 1 day, respectively.

Figure 10A:
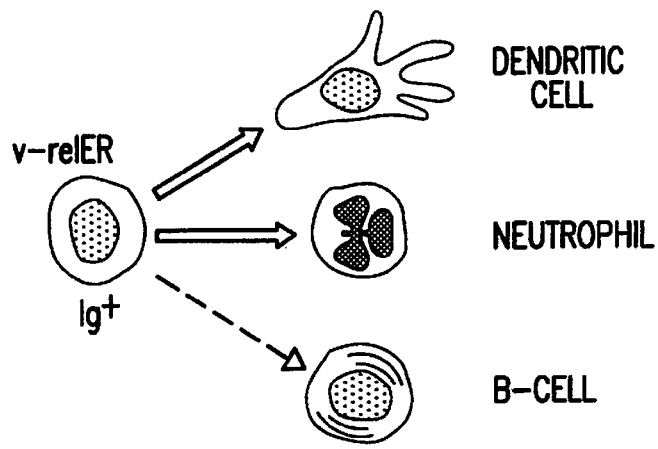
Figure 10B:
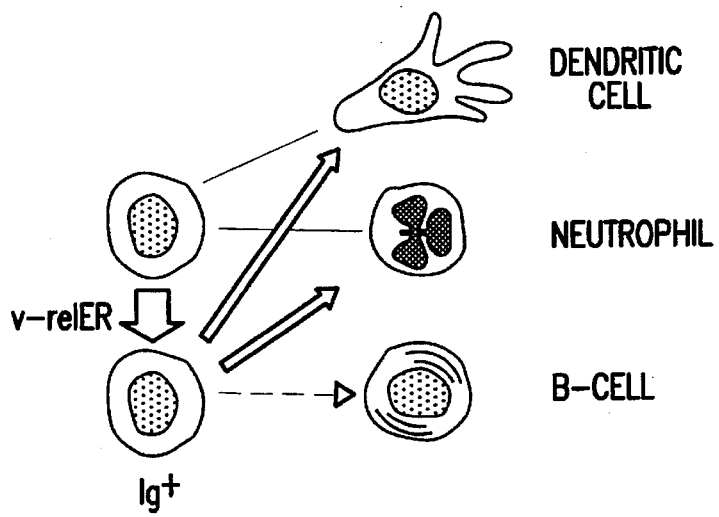
Figure 10C:
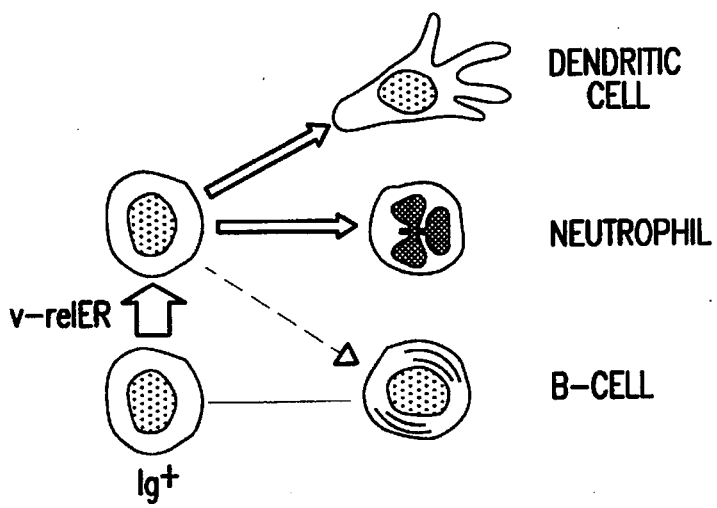

FIG. 10: Model for the differentiation potential of v-relER progenitors.

A) v-relER transforms a common progenitor for dendritic cells, neutrophils and B cells.

B) v-relER transformation of a common progenitor for dendritic cells and neutrophils induces expression of B-lymphoid determinants.

C) v-relER converts a B-lymphoid progenitor into a progenitor for dendritic cells and neutrophils.

Dark arrows indicate differentiation potential as described in this paper. Dashed arrows show that cells are expected to differentiate into mature B cells which, however, still remains to be demonstrated. Open arrows, shift in differentiation program due to the transforming oncogene (v-relER). Normal differentiation capacity (line). Ig$^+$ indicates that the respective cell has Ig genes rearranged.

Figure 11:
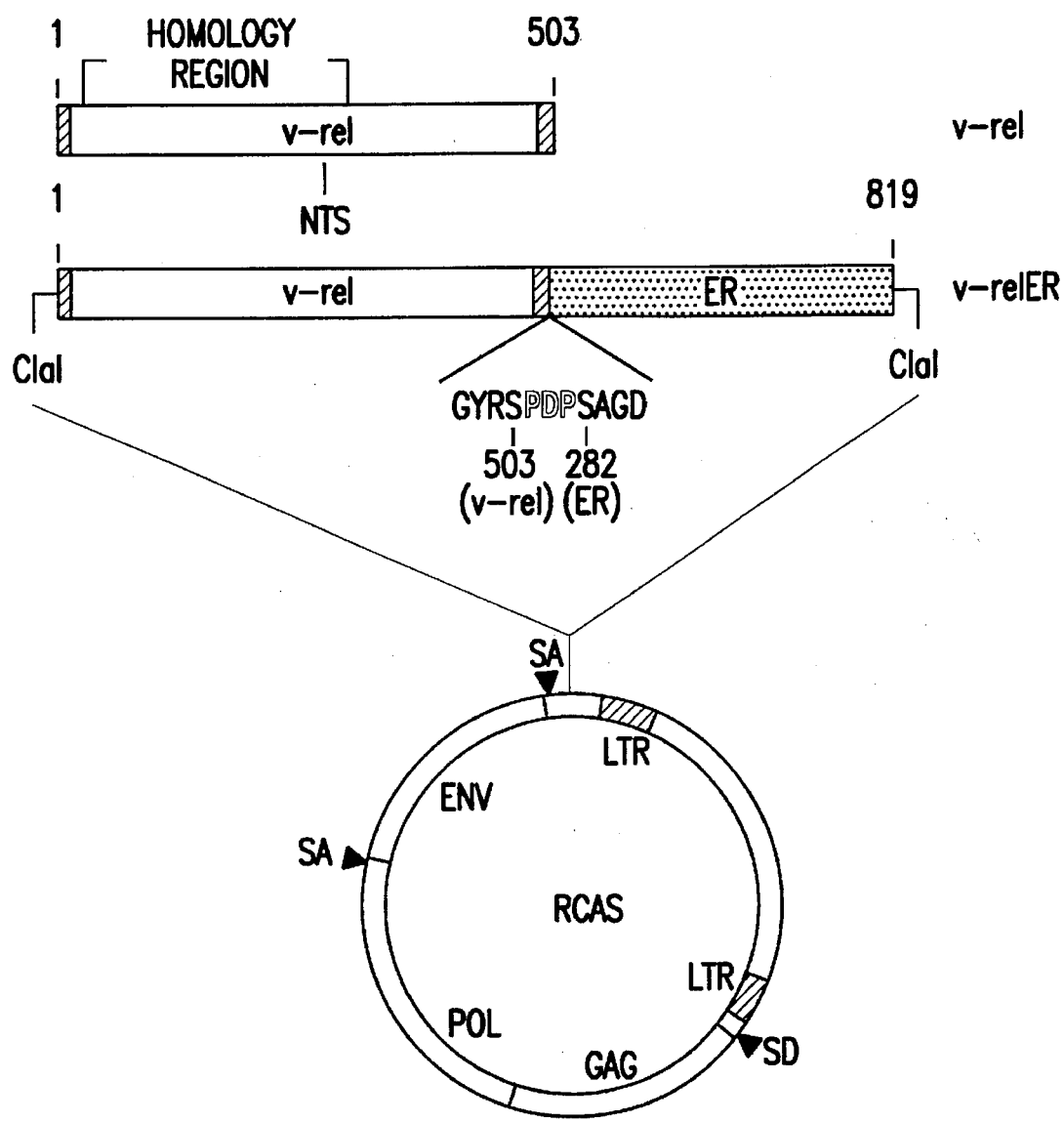

FIG. 11: Construction of a hormone-dependent v-relER fusion gene. A fusion of v-rel with the hormone binding domain (ER) of the human estrogen receptor was cloned into the ClaI site of the recombinant avian retrovirus RCAS. The amino acid sequence of the v-relER junction is shown. The retroviral long terminal repeat (LTR) sequences, splice donor and acceptor sites (SD and SA, respectively), the nuclear translocation signal (NTS) and the region of homology to other members of the NF-κB/rel/dorsal family (homology region) are indicated.

DETAILED DESCRIPTION OF THE INVENTION

The invention provides methods for inducing differentiation of transformed hematopoietic cells during culture. The method involves: introducing into the hematopoietic cells an oncogene capable of expressing an oncoprotein, wherein the oncoprotein is capable of transforming immature hematopoietic cells; culturing the cells in a first culture medium under conditions wherein the oncogene expresses the oncoprotein which promotes cellular growth while at least partially inhibiting cellular differentiation; deactivating the oncoprotein or expression from the oncogene to induce cellular differentiation; and culturing the cells in a second culture medium capable of supporting growth of differentiated hematopoietic cells.

A previously reported culturing system utilizing oncoprotein transformation of hematopoietic cells achieved proliferation of immature cells (Boehmelt et al., 1992). However, this study was limited because the proliferated cells remained undifferentiated. Large populations of differentiated hematopoietic cells are useful for screening potential immunomodulatory substances and vaccines. Thus, for the first time, the present inventors provide a method for inducing differentiation of such transformed immature hematopoietic cells during culture.

In one aspect, the present invention provides methods for producing differentiated cells from immature hematopoietic cells, said differentiated cells having morphological and functional characteristics of antigen-presenting dendritic cells. Preferably, the dendritic cells are highly mobile, fully differentiated antigen-presenting dendritic cells.

In another aspect, the methods of the invention provides methods for producing differentiated cells from immature hematopoietic cells, said differentiated cells having morphological and functional characteristics of polymorphonuclear neutrophils.

Oncogenes encoding oncoproteins capable of transforming immature hematopoietic cells are known in the art. For use in the present invention, the oncoprotein should promote cellular growth of the hematopoietic cells while at least partially inhibiting cellular differentiation. Candidate oncoproteins include those derived from members of the NF-κB family of transcription factors. For example, Narayanan et al. (1992) showed that a variant of the p65 subunit of NF-κB transforms rat embryo fibroblasts. The NF-κB family of transcription factors is well known in the art and is reviewed in Gilmore, 1991 and Bose, 1992. Other candidate oncoproteins include those derived from the Rel family (e.g., relB) of transcription factors. The Rel family proteins are related through an approximately 300-amino acid N-terminal domain, called the Rel homology domain, that contains sequences important for DNA binding, nuclear targeting, and dimerization (Capobianco and Gilmore, 1993). The NF-κB and Rel proteins are structurally related and functionally interact to regulate gene expression (Bose, 1992). It would be routine to select one of these known NF-κB or Rel proteins and test its suitability in the present invention by following the protocol set forth in the Example below.

Other candidate oncoproteins include Ela, Myc, Fos, Myb and the transcription factor C/EBP. The functions of each of these oncoproteins have been rendered hormone-dependent by fusion, at the genetic level, to sequences of a hormone receptor protein. (Picard et al., 1988; Eilers et al., 1989; Burk and Klempnauer, 1991; Superti-Furga et al., 1991; Umek et al., 1991). Preferably, the oncogene encodes a v-rel protein or a variant thereof. For example, the present inventors have discovered that both a wild type v-rel and a conditional v-rel variant (e.g., a v-rel/estrogen receptor fusion protein (v-rel/ER)), are capable of transforming immature hematopoietic cells and at least partially inhibiting cellular differentiation into more mature cell types. Oncogenes encoding both the wild type v-rel and the hormone-dependent variant v-rel/ER are described in Boehmelt et al., 1992 and Capobianco et al., 1993. In Boehmelt et al., the v-rel/ER variant was constructed as follows: PCR technology was used to generate a BglII site at the v-rel 3' end (adding 5'-CCAGATCT-3' at the nucleotide sequence encoding amino acid position 503 of v-rel). This was fused to the nucleotide sequence encoding amino acids 282–595 of the estrogen receptor hormone binding domain. Finally, the resulting construct was cloned into a retroviral vector.

The Capobianco et al. (1993) v-rel/ER construct encodes a fusion protein containing amino acids 1 to 438 of v-rel and amino acids 282–595 of the estrogen receptor with a 2 amino acid spacer. Thus, the skilled artisan will recognize that oncogenes encoding hormone-dependent fusion proteins for use in the present invention can be constructed which contain all or part of v-rel fused to all or part of a hormone receptor protein. Moreover, as indicated above, additional candidate oncoprotein/hormone receptor fusion proteins are described in Picard et al., 1988; Eilers et al., 1989; Burk and Klempauer, 1991; Superti-Furga et al., 1991; and Umek et al., 1991.

For the fusion proteins of the present invention, in a preferred embodiment, transformation activity is made dependent on the presence of estrogen or an estrogen agonist. Thus, in one aspect, the oncogene encodes a hormone-dependent fusion protein that induces cellular transformation only if the cells are cultured in the presence of a receptor-specific hormone. For example, the inventors have discovered that culturing fibroblasts and hematopoietic cells containing v-rel/ER in the presence of estrogen (about $10^{-9}$M to $10^{-6}$M) induces transformational-specific cellular proliferation and morphological changes. Alternatively, culturing in the presence of 4-hydroxytamoxifen (OHT) (about $10^{-10}$M to $10^{-7}$M) also induces cell transformation. As indicated, culturing the immature hematopoietic cells containing the fusion protein in the presence of estrogen or estrogen-agonist promotes cellular growth while at least partially inhibiting cellular differentiation. In fact, such v-rel/ER clones contained only about 0.5% elongated, bipolar cells (differentiated). Thus, while incomplete, the differentiation block provided by the fusion protein is highly significant. Moreover, the same degree of differentiation block was observed in clones containing the wild-type v-rel protein (which does not require hormonal presence for cell transformation).

In an alternative embodiment, transformation activity of the fusion protein can be made dependent on the presence of other hormones such as, but not limited to, dexamethasone or dexamethasone-agonists. This can be achieved by constructing an oncogene encoding a fusion protein containing all or part of one of the candidate oncoproteins described above fused to all or part of the glucocorticoid receptor. For example, in Umek et al. 1991, the CCAAT-enhancer binding protein (C/EBP) was fused to the glucocorticoid receptor (GR). Similarly, an oncogene encoding a v-relGR fusion protein would also be useful in the methods of the present invention. Hormone receptor proteins useful in the methods of the present invention are disclosed in Mattioni et al. 1994; Scherrer et al. 1993; and Jackson et al.

Because of the differentiation block provided by the oncoprotein activity, the oncoprotein must be deactivated to induce cellular differentiation. Deactivation may occur at the transcriptional, translational, or post-translational level either during or after culture in a first (growth) culture medium. Further, deactivation of oncoprotein activity may be physical (e.g., temperature control) or chemical (e.g., by addition of drugs). For example, if an oncogene encoding a wild-type oncoprotein is used to transform the hematopoietic cells, deactivation can occur by introducing into the cells an anti-sense construct complementary to the oncogene or to upstream transcriptional control sequences (such as the promoter). Such anti-sense constructs are known in the art. Alternatively, deactivation of a wild-type oncoprotein can occur post-translationally by introducing into the cells monoclonal antibodies specific for the oncoprotein. For example, if the v-rel oncoprotein is used, an anti-v-rel monoclonal antibody would be a suitable deactivator. Of course, methods for producing monoclonal antibodies are well known in the art.

In another embodiment, if an oncogene encoding a hormone-dependent fusion protein is used to transform the hematopoietic cells, deactivation can occur simply by removing the cells from the presence of the hormone. For example, if the fusion protein is estrogen dependent, culturing in media which is essentially estrogen-free will result in deactivation. Alternatively, an antagonist of the hormone can be used for deactivation. For example, the present inventors have discovered that culturing fibroblasts and hematopoietic cells in the presence of the anti-estrogen ICI 164,384 (ICI) ($10^{-9}$M to $10^{-6}$M) "switches-off" v-rel activity. Of course, other estrogen antagonist capable of interfering with estrogen binding to the estrogen receptor could also be used in addition to ICI. In another aspect, a nucleotide construct containing the oncogene encoding the fusion protein in anti-sense orientation could also be used for deactivation. Such a construct is described in the Example below.

By the invention, in another preferred embodiment, an oncogene that encodes a temperature-sensitive (ts) mutant can be used provided that the protein is capable of transforming immature hematopoietic cells. Preferably, the ts mutant is a v-rel variant. Such a construct can be generated using any suitable mutagenesis technique. For example, in White and Gilmore, 1993, a ts v-rel mutant was constructed by altering certain nucleotides in the wild type construct using site directed mutagenesis. The resulting construct was cloned into plasmid vectors and electroporated into cells. At a permissive temperature, the ts v-rel construct produced oncoproteins which transformed the cells. However, at an elevated non-permissive temperature, the activity was not observed.

Thus, in another aspect, the present invention encompasses introducing a ts v-rel oncogene into hematopoietic cells wherein the gene product is capable of transforming immature hematopoietic cells. Permissive temperatures for culture in the first culture medium can be determined empirically. However, temperatures ranging from about 35°–38° C. should be permissive.

Deactivation of the ts oncogene product can occur simply by raising the temperature to a non-permissive level. Non-permissive temperatures can be determined empirically. Temperatures at or above about 41° C. should be non-permissive.

By immature hematopoietic cells is intended undifferentiated bi- or multi-potent cells. These include, stem, progenitor and precursor cells. Phenotypic and functional assays for characterizing immature hematopoietic cells are known in the art. For example, cytometric analysis using monoclonal antibodies specific for cluster determinant (CD) antigens can be used for phenotypic identification of immature hematopoietic cells. Such antibodies can be conjugated with either fluorescein isothiocyanate (FITC) or phycoerythrin (PE). Monoclonal antibodies specific for the CD34, CD38, CD20, CD14, CD3, CD4, CD16, CD15, HLA-DR, CD33, CD11 b, and CD8 antigens are available from Becton Dickinson Monoclonals, San Jose, Calif. The presence of hematopoietic progenitor subpopulations (CFU-MIX; CFU-GM; BFU-E; CFU-Blast; CFU-Mk) can be determined using methylcellulose CFC (colony forming cell) assays as described in Meisenberg, 1992. Finally, the methods described in the Example below can be used for characterizing undifferentiated hematopoietic cells.

Sources of hematopoietic cells include umbilical cord blood cells, bone marrow cells, and peripheral blood cells. These cells can be obtained from vertebrates, preferably birds or mammals. If cells of avian origin are used, chicken is preferred. Preferred mammalian species are mouse and man. Isolation procedures are known in the art (Morrison et al., 1991).

By the invention, the transformed hematopoietic cells are cultured in a first culture medium under conditions wherein the oncogene expresses an oncoprotein which promotes cellular growth while at least partially inhibiting differentiation into more mature cells. The first culture medium can be any culture medium known in the art as suitable for culturing transformed bone marrow cells and which is compatible with the conditions necessary for oncogene regulation. For example, the growth media described in the Example below is based on a standard growth medium (DMEM) supplemented with animal serum. Other standard growth media are well known in the art and include, but are not limited to, IMDM, RPMI 1640 and AIM-V. If the hematopoietic cells are from chicken, the standard growth medium should be supplemented with fetal calf serum (FCS) (2.5–10%) and chicken serum (ChS) (2–10%). Thus, the standard growth medium should be supplemented with FCS and other animal serum depending on the origin of the hematopoietic cells. For example, if rabbit or human hematopoietic cells are used, the standard growth medium should be supplemented with FCS and rabbit or human serum, respectively.

After culture in the first (growth) culture medium, the cells should be cultured in a second (differentiation) culture medium which fits the needs of the type of differentiated cells to be produced. For production of dendritic cells, a second culture medium based on a standard growth medium as described above supplemented with transferrin (e.g., chicken conalbumin) and/or insulin is preferred. This medium may contain transferrin at a concentration of 1 to 1000 µg/ml and insulin at a concentration of 0.01 to 1 µg/ml. To obtain highly mobile antigen-presenting dendritic cells, this medium should be further supplemented with fibroblast conditioned medium (e.g., the CCE-medium described in the Example below). The fibroblast conditioned medium can be included at concentrations of 20 to 100%. Thus, by the invention, dendritic cell differentiation can also be induced when fibroblast conditioned medium is fully substituted for the standard growth medium. Alternatively, highly mobile antigen-presenting dentritic cells can be obtained by pre-treating ("coating") culture dishes with fibroblast conditioned medium and culturing the cells in the presence of standard growth medium supplemented with transferrin and insulin (and ICI if the oncoprotein is an estrogen-dependent fusion protein).

A second culture medium based essentially on CFU-E medium (Radke et al., 1982) is well-suited for the production of cells having properties of polymorphonuclear neutrophils. For example, a CFU-E medium containing DMEM supplemented with the following components can be used: FCS (2.5–10%), chicken serum (2–10%), detoxified BSA 1–15 mg/ml, β-mercaptoethanol (10–150 µM), sodium bicarbonate (1.9 mg/ml), conalbumin (50–200 µg/ml) and insulin (0.03–1 µg/ml). This medium may be modified as needed. For example, if mammalian cells other than chicken cells are used, then the corresponding mammalian serum (e.g., rabbit or human) can be substituted for the chicken serum recited above.

By the invention, oncogenes can be introduced into the hematopoietic cells according to any suitable technique. These include, but are not limited to, electroporation, injection of "naked" or liposomally- encapsulated DNA, and transduction with packaged virions. As the Example below shows, the present inventors cloned an oncogene encoding the v-rel/ER fusion protein into the replication competent retrovirus vector RCAS (Hughes et al., 1987) thereby generating RCASv-rel/ER. RCASv-rel/ER DNA or wild-type v-rel DNA was then transfected into chicken fibroblasts. To infect hematopoietic cells, the virus-producing chicken-fibroblasts were co-cultivated with bone marrow cells for approximately one day. Of course, the oncogenes could also be introduced into the hematopoietic cells using replication-incompetent viral vectors.

Such vectors are commonly produced from packaging cells lines. In general, packaging cell lines which produce packaged virions capable of transducing vertebrate hematopoietic cells are well known in the art. Packaging cell lines contain retrovirus-derived DNA that supplies the necessary gene functions, such as the env gene, for viral packaging. For example, if the hematopoietic cells are human, packaging cell lines derived from NIH 3T3 cells, and particularly from NIH 3T3 (Tk⁻) cells, can be used. A DNA construct, such as a plasmid, containing the retroviral sequences with the desired deletions and mutations and a selective marker, such as the herpes simplex virus (HSV) thymidine kinase (TK) gene are introduced into the cell line and cultured in selective medium. Cells, which grow in the selective medium, are selected and tested for the presence of the necessary packaging functions. Those that produce retroviral vectors and do not produce helper virus are selected and used as packaging cells lines to produce infectious replication-incompetent retroviral vectors.

Thus, in an alternative introduction method, the oncogene could be contained within packaged virions produced from a PA-317-derived packaging cell line (if the hematopoietic cells are human) known in the art. The packaged virions could then be used to transduce the human hematopoietic cells thereby introducing the oncogene. If replication defective virus is used, the cells may also be infected with helper virus.

As indicated above, the cell differentiation system for hematopoietic cells, especially dendritic cells, described in this application overcomes limitations of the prior art. For example, clonal and homogenous cell populations of v-relER progenitors are readily available in large cell numbers. By the invention, such cells can be propagated in culture for several months and will give rise to fully functional dendritic cells over the entire duration of culture. Moreover, the accessibility of clonal populations of dendritic cell precursors and their differentiated progenies allows, for the first time, analysis, by differential cDNA cloning strategies, the gene expressional repertoire responsible for the dendritic differentiation program.

Furthermore, using the methods of the invention, it is now possible to assess whether distinct subtypes of dendritic cells (e.g., follicular dendritic cells) can be obtained from a bone marrow derived precursor cell by providing an appropriate microenvironment in vivo (e.g., by injection of labelled v-relER progenitors into various lymphoid and non-lymphoid organs). Such studies might possibly resolve the issue as of the bone marrow versus mesenchymal origin of follicular dendritic cells (for a review see Heinen and Bosseloir, 1994).

In a further aspect, differentiated hematopoietic cells generated by the methods of the present invention are useful for screening potentially immunomodulatory substances or in the development of vaccines. Moreover, efficient antigen-presentation on dendritic cells can be achieved by peptide/protein pulsing in vitro or by their genetic modification following gene transfer. The present inventors have performed experiments which demonstrate efficient gene transfer in vitro into dendritic cells of chicken, mouse and human.

Having generally described the invention, the same will be more readily understood through reference to the following example which is provided by way of illustration and is not intended to be limiting.

EXAMPLE

Production of fully competent dendritic cells and cells resembling polymorphonuclear cells from chicken bone marrow cells Experimental animals White Leghorn chickens (originally derived from the SPAFAS flock and maintained at IMP in Vienna, Austria) were used. Lohmann Brown chickens were obtained from a commercial breeder and used for the mixed lymphocyte reaction.

Recombinant plasmid vector coding for v-relER fusion protein (Boehmelt et al, 1992)

Construction of RCASv-relER. PCR technology was used to generate a BglII site at the v-rel 3' end (adding 5'-CCAGATCT-3' at amino acid position 503) of pBSrelCS (Morrison et at., 1991). In v-relER this BglII site is fused to the estrogen receptor hormone binding domain (ER; amino acids 282–595) contained in a BamHI-SacI fragment of recombinant HE14 (Kumar et al., 1986). The amino acid sequence generated at the v-rel/ER junction is shown in FIG. 11. Finally, the v-relER fusion gene was cloned as a ClaI fragment into the unique ClaI site of pRCAS (Hughes et al., 1987) thereby generating pRCASv-relER and pRCAS-anti-v-relER, containing v-relER in the sense or antisense orientation, respectively.

Bone marrow cell transformation (Boehmelt et al., 1992)

Bone marrow from 4–7 day old chickens was isolated as described (Morrison et al., 1991). For infection, bone marrow cells were cocultivated with virus-producing, v-rel-or v-relER-transformed, mitomycin C treated (5 µg/ml; 1–2 h) fibroblasts for 24 h, in either the presence or absence of $10^{-6}$M estrogen. CFU-E medium (Radke et al., 1982) supplemented with 1 µg/ml human recombinant insulin and 1% anemic chicken serum was used.

The outgrowth of v-relER-transformed bone marrow cells occurred between days 11 and 14 after infection. Cells were then adapted to standard medium conditions (see below). In rare instances, an outgrowth of v-relER-transformed bone marrow cells was obtained in the absence of estrogen. In such cells, v-relER had apparently undergone extensive deletions within or of the entire estrogen receptor hormone binding domain (data not shown). Such cells were not further analyzed.

For selection clones of v-relER-transformed bone marrow cells, aliquots of a v-relER mass culture were seeded into CFU-E methocel. Individual colonies were isolated 7 days later and expanded in standard growth medium containing $10^{-6}$M estrogen.

Cell culture

V-rel and v-relER transformed cells, normal bone marrow macrophages, chicken embryo fibroblasts (CEFs) and chicken cell lines (e.g., RP9, Beug et al., 1981) were grown in standard growth medium (EBM) containing Dulbeceo's modified Eagle's medium (DMEM) supplemented with 8% fetal calf serum (FCS), 2% chicken serum (ChS) and 20 mM HEPES pH7.3.

Medium I consisted of standard growth medium supplemented with conalbumin (130 µg/ml) and human recombinant insulin (Actrapid Novo Nordisk, 0.1 µg/ml) and was used to induce differentiation of v-relER cells into dendritic cells. Medium II represents a modified CFU-E medium (Radke et al., 1982) and contains DMEM supplemented with 8% FCS, 5% ChS, 8 mg/ml detoxified BSA, 1.9 mg/ml sodium bicarbonate, 0.12 mM β-mercaptoethanol, 130 µg/ml conalbumin and 0.1 µg/ml human recombinant insulin. Medium II was employed to differentiate v-relER cells into the neutrophil phenotype. Medium II supplemented with 10 ng/ml TGFα (transforming growth factor type α; Promega) and $10^{-6}$M 17-β estradiol (Sigma) but without insulin was used to obtain normal TGFα-dependent erythroid progenitor cells according to protocols described before (Schroeder et at., 1993).

MLR medium contained DMEM supplemented with 1% heat inactivated FCS, 2.5% heat inactivated ChS, 2 mM glutamine, $5 \times 10^{-5}$M β-mercaptoethanol and 10 mM HEPES pH7.3. The medium used to achieve high levels of surface IgM expression in v-relER cells was DMEM supplemented with 8% FCS, 5% ChS, 130 µg/ml conalbumin, 20 mM HEPES pH7.3 and human recombinant insulin (0.1 µg/ml) containing $10^{-6}$M 17-β estradiol and 20 ng/ml phorbol 12-myristate 13-acetate (PMA, Sigma). CCE-medium (CEF-conditioned EBM) was used to induce adherence of v-rel and v-relER cells. To obtain CCE-medium, primary CEFs were grown for 2–3 days in standard growth medium; the culture supernatant was recovered and sterile filtered (0.45 µm). CCE medium most probably induces adherence via an extracellular matrix component rather than a soluble factor, since adherence of v-rel and v-relER cells was also obtained in normal growth media, provided that the tissue culture dish was pretreated with CCE-medium.

17-β estradiol (Sigma) and ICI164.384 (ICI; Dauvois et al., 1992; Wakeling et Bowler, 1988; Bowler et al., 1989; kindly provided by Dr. A Wakeling, ICI, England) were dissolved in ethanol at 1 mM final concentration and stored at −20° C. These compounds were administered daily as specified before (Boehmelt et al., 1992).

Histochemical staining

Histochemical staining was performed as described by the manufacturer. May-Grünwald/Giemsa staining (Merck or Fluka) was done on air-dried, methanol-fixed cytospin preparations.

Sudan Black B staining (Sigma) was originally described by Sheehan and Storey (1947). Human peripheral blood neutrophils used as a positive control showed a characteristic staining pattern, whereas chicken bone marrow cells, smears of chicken peripheral blood and cytospin preparations of undifferentiated and differentiated v-relER cells were consistently found to be negative.

Periodic acid-Schiff (PAS) reagent (Sigma) was used to detect glycogen which represents the major energy source in mature neutrophils. While in human neutrophils (used as a positive control) a homogeneous staining was observed (Zucker-Franklin et al., 1988), neutrophil v-relER cells exhibited an apparently atypical vesicular staining pattern.

Acid phosphatase staining was employed to discriminate dendritic v-relER cells (grown in CCE-medium) from macrophages. Therefore cells were washed in phosphate buffered saline (PBS), fixed in 3% paraformaldehyde (10 min, room temperature), rinsed with PBS and subjected to acid phosphatase staining directly on the tissue culture dish. Acid phosphatase converts Naphtol-ASBI phosphate (Sigma) into a red adduct, if incubated for 1 hour at 37° C. in a solution containing 150 µl Naphtol-ASBI phosphate (10 mg/ml in N-N dimethyl formamide), 1.8 ml 0.1N acetate buffer pH5.2, 750 µl veronal buffer (17 g/100 ml sodium acetate, 2.6 g/100 ml 5,5-diethylbarbituric acid), 120 µl pararosaniline (Sigma, 1 g dissolved in 20 ml $H_2O$ plus 5 ml 12N HCl) and 120 µl of 40 mg/ml $NaNO_2$ (modified from Barka and Anderson, 1962). Following incubation specimens were rinsed in $H_2O$ and photographed.

Immunofluorescence analysis

To reveal expression of specific surface antigens, cells were subjected to life cell immunofluorescence (Beug et al., 1979). The monoclonal antibodies MC47-83, MC51-2, MC22-3 and the polyclonal lymphoid-specific rabbit serum REV3118a were used as described in Morrison et al. (1991). The CB10, CLA3, Hy86B5 and 5M19 antibodies were kindly provided by Dr. D. L. Ewert, Wistar Institute, Philadelphia, USA and used as described in Olson and Ewert (1990). The antibody 4M12-26 is described in Kornfeld et al. (1983). The monoclonal antibody M-1 (Chen et al., 1982) specific for chicken surface IgM was kindly provided by Drs. C.-L. Chen and M. D. Cooper (University of Birmingham, Birmingham, Ala., USA) and used in a 1:100 dilution. For analysis of chicken MHC class II expression, the monoclonal antibody 2G11, specific for the nonpolymorph region of the chicken B-L (MHC II) B-chain (Kaufman et al., 1990), was used (1:40 dilution).

As secondary antibodies FITC-conjugated goat anti-rabbit IgG F(ab')$_2$ fragment (Tago) and FITC- or TRITC-conjugated goat-anti-mouse serum (Sigma) were used to detect the rabbit and mouse antibody complexes, respectively. Antibody incubation was for 45 min at room temperature with dilution 1:50. Finally cells were mounted in antifade solution (80% glycerol supplemented with 10 mg/ml 1,4-phenylene diamine-dihydrochloride in carbonate buffer pH8.0 [4.2 g/100 ml NaHCO$_3$+5.3 g/100 ml Na$_2$CO$_3$] containing 0.5 μg/ml DAPI (Sigma) to stain nuclei.

Alternatively, 10$^6$ cells were stained with the respective first and secondary antibodies, propidium iodide (Sigma) was added (2 μg/ml final concentration) and cells were analysed using a FACScan. (Becton Dickinson) by gating on forward and side scatter.

Immunofluorescence analysis on adhesion slides

Adhesion slides (Bio-Rad) were used according to the manufacturer's specifications to maintain the natural shape of nonadherent cells during immunofluorescence analysis. 7×10$^4$ nonadherent cells were washed in PBS and allowed to adhere to marked areas on adhesion slides (5 minutes, room temperature). Subsequently, adherent cells were rinsed with PBS, fixed (3% paraformaldehyde in PBS for 15 min at room temperature) and permeabilized with 0.5% NP40 in PBS (15 min, room temperature). Following 3 washes with PBS, fixed cells were incubated with the appropriate antibody (20 μl/sample, 60 minutes).

For analysis of vimentin expression, the monoclonal anti-vimentin antibody vim3B4 (Boehringer Mannheim, Germany) was used in a 1:100 dilution. FITC-conjugated goat-anti-mouse IgG (Sigma; diluted 1:40) was employed for detection. Finally, cells were mounted in antifade solution supplemented with DAPI (see above).

Image processing

Fluorescence was visualized using a Zeiss Axiophot microscope equipped with a cooled charged coupled (CCD) camera (Photometrics, KAF 1400–50) which was controlled by an Apple Macintosh computer. Images were recorded sequentially using specific filter settings for fluorescine, DAPI and rhodamine. They were then processed to pseudo-colored images using the Gene Join program (T. Rand, Yale, USA). Representative areas were arranged to figures using the Enhance program. Final images were obtained by producing prints from merged image files using the McRasQ program.

Electron microscopy

The cells were washed once in PBS and fixed in 2.5% glutaraldehyde in PBS. Subsequently, cells were embedded in 2% agarose, postfixed in.1% osmium tetroxide for 1 hour at 4° C., rinsed in H$_2$O and stained with 1% aqueous uranylacetate (1 hour at 4° C.). Specimens were then dehydrated in a graded series of ethanol and finally embedded in Epon. Inspection was performed with a Philips CM-10 electron microscope on ultrathin sections which were finally stained with uranylacetate and lead citrate.

Time-lapse photography

To demonstrate the high mobility of dendritic v-relER cells, time-lapse cinemicroscopy was employed. A Zeiss Axiovert 35 microscope equipped with a small incubator and a CCD video camera (Sony) connected to an optical disc facility (Laser Videodisc Recorder LVR-6000A, Laser Videodisc Processor LVS-6000AP, Sony) was used. Cells incubated on 60 mm tissue culture dishes in a humidified atmosphere containing 5% CO$_2$ at 37° C. were photographed automatically in regular time intervals as indicated. To avoid condensation, agarose coated lids were used. Records were displayed on a high resolution black and white monitor and photographed.

Phagocytosis assay

2×10$^6$ cells were washed in standard growth medium followed by incubation in 1 ml standard growth medium containing 2.5 μl TRITC-labeled latex beads (diameter: 0.48 μm; Polysciences Inc.). The cells were incubated for 1 hour at 37° C. in a humidified atmosphere. Subsequently, cells were washed twice with 10 ml PBS, resuspended in 200 μl PBS and fixed by addition of 1 ml methanol (5 minutes, room temperature). Fixed cells were washed in 10 ml PBS, centrifuged (1500 rpm, Heraeus Minifuge RF), resuspended in 20 μl antifade solution containing DAPI (see above) and mounted onto slides. Adherent cells (bone marrow macrophages) were detached from the tissue culture dish by EDTA treatment prior to analysis for phagocytic activity. Finally, cells were investigated by fluorescence microscopy.

Mixed lymphocyte reaction (MLR)

Several attempts to achieve a stimulation of naive T-lymphocytes by using antigen-presenting cells from peripheral blood, thymus or spleen of different Whim Leghorn SPAFAS chickens (maintained at IMP, Vienna) failed. This is probably because this chicken flock is inbred for more than 15 years to date and hence has only a limited potential of alloreactivity. Therefore spleen cells were prepared from Lohmann Brown chickens (obtained from a commercial breeder) and used for the MLR.

Spleen suspension cells were generated by carefully removing the connective tissue capsule of the spleen and squeezing the spleen tissue through a stainless steel mesh. Erythrocytes were removed by low speed centrifugation (in PBS containing 1% heat inactivated FCS) followed by Ficoll Hypaque purification (Eurobio, Paris, density 1.077 g/ml). All following washing steps were performed in standard growth medium containing heat inactivated chicken serum and FCS (in the following referred to as HI-medium). For mitomycin C treatment (25 μg/ml) spleen stimulator cells were incubated in HI-medium for 45 minutes at 39° C.; v-rel or v-relER stimulator cells were treated similarly in their respective culture medium. Following mitomycin C treatment, cells were washed 3 times with HI-medium and twice in MLR medium (see above). Viability of cells was evaluated by trypan blue (Sigma) exclusion and/or cytospin preparations.

For the MLR-assay, 5×10$^4$, 10$^5$ and 2.5×10$^5$ responder cells were incubated with an increasing number of mitomycin C-treated stimulator cells in 100 μl MLR medium in 96-well dishes as indicated. Best results were obtained with 2.5×10$^5$ responder cells. As a control, responder cells were treated with 1–5 μg/ml concanavalin A (ConA, Pharmacia) or 20 ng/ml phorbol-12-myristate-13-acetate (PMA, Sigma). Following incubation for 78–88 hours at 39° C., cells were labeled with 0.8 μCi $^3$H-thymidine (specific activity 29 Ci/mmol; Amersham) for an additional 18 hours. Labeled cells were harvested on filtermates using an automated 96-well harvester (Tomtec). Dried filtermates were subsequently covered with scintillation wax and measured employing a Microbeta 1450 Liquid Scintillation Counter (Wallac, Turku, Finland). The $^3$H-thymidine incorporation of ConA- or PMA-treated control cells was in the range of 6000–15000 cpm; mitomycin C treated cells or responder cells alone exhibited background incorporation (100–400 cpm).

To obtain normal dendritic cells, chicken spleen cell suspensions were prepared as described above. Cell suspensions were washed two times in standard growth medium, followed by high speed centrifugation (20 min, 4500 rpm) through a Percoll cushion (density 1.085 g/ml). The light density fraction was washed once in standard growth medium and cells were seeded at high density (3–5×10⁶ cells/ml) for 8–18 hours. Subsequently, nonadherent cells were carefully removed. Adherent cells represented a mixture of strongly adherent macrophages, loosely adherent cells with large denrite-like protrusions and highly mobile "veiled" dendritic cells (modified from a protocol for enrichment of dendritic cells from mouse spleens; Steinman et al., 1979).

Western blotting

Protein detection by immunoblotting was performed as described in Boehmelt et al. (1992) with the following modifications: To more efficiently block nonspecific binding of antibody, the concentration of gelatine in PBS was increased to 1.5%. The polyclonal antibody raised against chicken min-1 protein (kindly provided by Drs. S. Ness and T. Graf, EMBL, Heidelberg) was used in a 1:1000 dilution. After five washing steps the nitrocellulose membrane was incubated with a 1:5000 dilution of horseradish peroxidase-conjugated donkey-anti-rabbit IgG in PBS. For detection of the antigen/antibody complex the ECL chemiluminescence kit (Amersham, England) was used according to the manufacturer's specifications.

Cloning of chicken BSAP and RNase protection analysis

Part of the chicken BSAP cDNA was cloned from the chicken B cell line RPL-12 using redundant oligonucleotide primers (a and b, see below) as described for cloning of human and mouse BSAP (Adams et al. 1992). The fragment obtained encodes part of the paired domain corresponding to amino acids 71–114 in murine and human BSAP and exhibits perfect homology on the amino acid level. This chicken BSAP-specific cDNA fragment was subsequently cloned in an antisense orientation into the polylinker of the vector pSP64 (Promega) to obtain BSAP-specific SP6 probes. RNase protection analysis was carried out according to Vitelli et al. (1988). Primer sequences were (a) 5'-GCG GAA TTC AGR TAY TAY GAR ACN GGN AGY AT-3' (SEQ ID NO: 1) and (b) 5'-GCG GTC GAC RAT YTC CCA NGC RAA CAT NGT NGG-3' (SEQ ID NO: 2).

Nuclear extracts and EMSA

Nuclear extracts were prepared according to Schreiber et al. (1989) except that protease inhibitors were added to the extraction buffer (see Barberis et al., 1990). Electrophoretic mobility shift assays (EMSA) were described before (Barberis et al., 1990). For competition experiments, 1 pmol unlabelled oligonucleotide (H2A-2.2 wild-type or mutant, respectively, Barberis et al., 1990) was included in the DNA binding reaction. Alternatively, 0.2 µl of rabbit anti-murine BSAP antiserum, directed against the paired domain, was used (Adams et al., 1992). Oligonucleotide sequences were: (wtH2A-2.2) 5'-CAG GGT TGT GAC GCA GCG GTG GGT GAC GAC TGT CGG-3' (SEQ ID NO: 3) and (mutH2A-2.2) 5'-CAG GGT TGT GAC GAA GCG GTG GGT GAC GAC TGT CGG-3' (SEQ ID NO: 4).

Analysis of v-relER cells grown in the presence of estrogen

Previous work demonstrated that a conditional v-rel estrogen receptor fusion protein (v-relER) transforms chicken bone marrow cells in vitro in a strictly estrogen-dependent manner (Boehmelt et al., 1992). Subsequently, several v-relER transformed bone marrow cell clones were isolated and expanded in liquid culture in the presence of estrogen. On the basis of morphological criteria, such cells appeared to be identical to cells transformed by wild type v-rel (Boehmelt et at., 1992, see also below FIG. 1). This result was confirmed when v-rel transformed cells and cells containing the hormone-activated v-relER were analysed for expression of a series of cell type-specific surface markers. Table 1 shows that expression of a panel of myelomonocytic surface antigens (as detected by a series of monoclonal antibodies) is either high (MC47-83, 4M 12-26 and 5M 19) or absent (MC51-2, MC22-3) on both v-rel and v-relER transformed bone marrow cells. Additionally, both v-rel and v-relER cells expressed two lymphoid surface markers (Hy86B5, REV3118a) and the CLA-3 antigen with virtually identical frequency and intensity (Table 1). Conversely, CB10, an antigen present on 97% of bursal lymphocytes and on cells of the monocytic lineage (Olson and Ewert, 1990) was neither detected on v-rel, nor v-relER transformed cells (data not shown). All v-relER cell clones studied express surface IgM and high levels of MHC class II antigen (Table 1), as described before for v-rel transformed cells (Barth et al., 1990 and Benatar et at., 1991, and references therein).

Thus, our studies demonstrate that clonal cell populations of v-relER transformed bone marrow cells, grown in the presence of estrogen, coexpress myeloid and lymphoid markers, in line with previous studies on v-rel transformed cells (Barth et al., 1990; Morrison et al., 1991; Bose, 1992).

Table 1: Surface antigen expression of v-rel and v-relER transformed cells. Life cell immunofluorescence was performed with v-rel and v-relER transformed cells grown in standard growth medium supplemented with estrogen (v-relER). A panel of monoclonal antibodies specific for myelomonocytic cells (MC47-83, 4M12-26, 5M19, MC51-2) and lymphoid cells (Hy86B5) was employed. The monoclonal antibody CLA-3 reacts with all leukocytes (*)while the polyclonal rabbit serum REV3118a recognizes lymphoid cells only. Surface IgM expression was detected using the monoclonal M-1 antibody and FACS analysis. MHC class II expression was revealed by the monoclonal antibody 2G11 (specific for the nonpolymorph region of the chicken B-L β-chain). The percentage of positive cells was evaluated by analyzing 400–900 cells. Average values from at least two independent experiments are shown. Weak but distinct immunofluorescence (+), strong and very strong immunofluorescence (++ and +++, respectively), no positive cells (−). The percentage of positively stained cells within a given cell population is indicated in parenthesis.

| surface antigen expression | | v-relER | | v-rel | |
|---|---|---|---|---|---|
| myeloid | MC47-83 | ++ | (90) | ++ | (60) |
| | MC51-2 | − | | − | |
| | MC22-3 | − | | − | |
| | 4M12-26 | ++ | (100) | ++ | (100) |
| | 5M19 | + | (100) | + | (100) |
| lymphoid | Hy86B5 | +++ | (100) | +++ | (100) |
| | REV3118a | ++ | (90) | ++ | (80) |
| | Cla3(*) | + | (95) | + | (95) |
| MHC class II | 2G11 | +++ | (100) | +++ | (100) |

Generation of differentiated cells from v-relER cells.

For the generation of differentiated cells from v-relER cells, v-relER oncoprotein was first "switched off" by addition of the estrogen antagonist ICI 164.384 (ICI). Several independent v-relER bone marrow cell clones were expanded in the presence of estrogen and following addition of ICI evaluated for their potential to differentiate.

First, incubation of v-relER cell clones in a modified standard growth medium (supplemented with conalbumin and insulin; medium I) and ICI resulted in the appearance of characteristic elongated cells (FIG. 1). May-Gr ünwald/Giemsa staining of these cells revealed a polarized morphology, characterized by vacuolized, reddish cytoplasm confined to one side of the cell body and smooth, bluish cytoplasm at the opposite side (FIG. 1). Such elongated, bipolar cells were also obtained when differentiation was induced in normal standard growth medium and ICI, however, differentiation was less efficient due to an increased rate of cell death. Secondly, the same v-relER cell clones cultured with ICI under different media conditions (a modified CFU-E medium, Radke et al., 1982; medium II) yielded a second morphologically distinct cell type: These cells were spherical, unpolarized and contain segmented, polymorphic nuclei. The cytoplasm was without preference for basophilic or eosinophilic dyes (FIG. 1).

Cells transformed by wild type v-rel did not respond to ICI treatment and remained virtually unchanged morphologically under all conditions tested (FIG. 1A). We have noted, however, that several v-rel cell clones and all v-relER clones (in the presence of estrogen) contained about 0.5% of elongated, bipolar cells when grown in standard growth medium (data not shown). This observation indicates that the differentiation block achieved by v-rel or hormone-activated v-relER is incomplete.

Figure 2B:
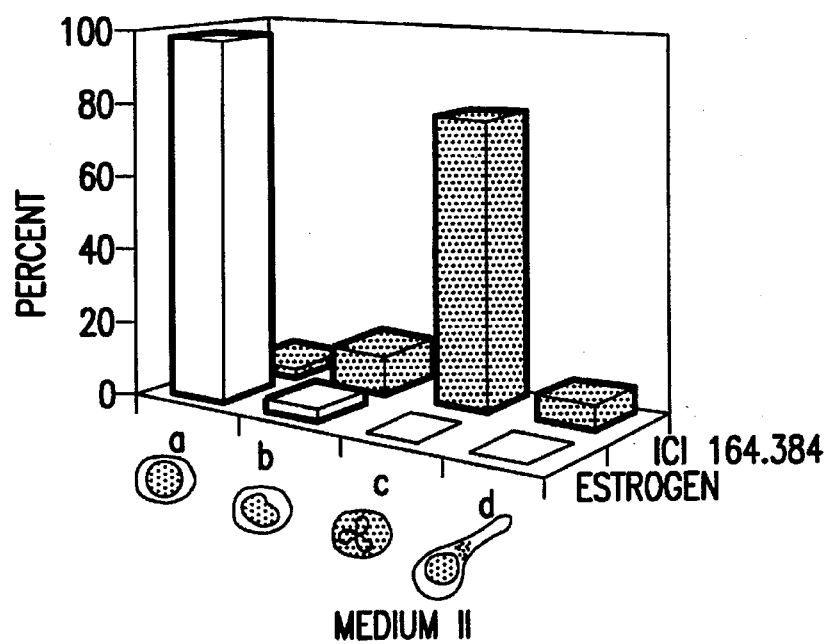
Figure 3A:
FIG. 3: Ultrastructure of differentiated v-relER cells. Electronmicroscopic analysis was performed using transformed v-relER cells (A), dendritic v-relER cells obtained in medium I (B, D, E, F) and v-relER cells phenotypically reminiscent of mammalian neutrophils (C). Please note the intracellular polarization and the long cytoplasmic processes visible in longitudinal sections of differentiated dendritic v-relER cells (B, D). Although v-relER cells differentiated in medium II (C) lack electrondense granules they are considered as chicken neutrophils due to their characteristic multilobed nucleus. In panels A-C cells are depicted at identical magnification (×8300) to reveal their relative size. The basal side of a dendritic v-relER cell (E, F) contains mitochondria, Golgi-apparatus, vesicles, microtubuli (black arrows in F), membranous vacuoles, ribosomes and bundles of intermediate filaments (open arrows in E, F). The cytoplasm on the opposite side is devoid of any subcellular structures besides ribosomes (D). Panels D and E show details of the cell depicted in B at higher magnification (×18300); the basal cytoplasm shown in panel F (×24800) refers to another dendritic v-relER cell. Black triangle indicates budding virus.
Figure 3B:
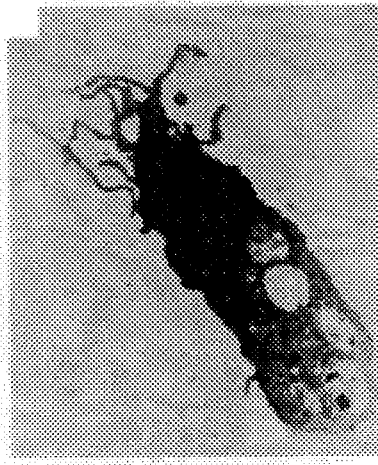
Figure 3C:
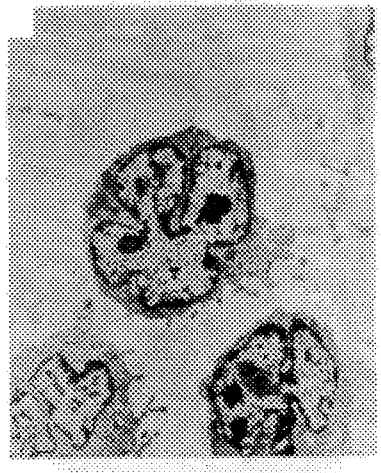
Figure 3D:
Figure 3E:
Figure 3F:
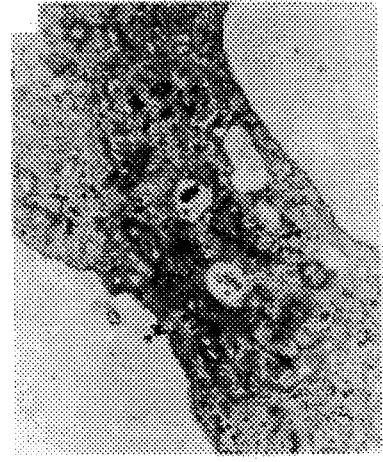

FIG. 2 summarizes the relative proportion of differentiated v-relER cells obtained in the presence of medium I or medium II, respectively. As can be seen, differentiation into characteristic cell types was critically dependent on the specific culture conditions used. In medium I >85% of the cell population differentiated into elongated, bipolar cells, while the remaining cells failed to terminally differentiate (FIG. 2A). In contrast, differentiation in medium II yielded about 80% of cells exhibiting the characteristic polymorphonuclear phenotype, about 10% of elongated cells and a minor proportion of undifferentiated cells (FIG. 2B). This behavior was found for all v-relER clones tested (8/8). While differentiation in medium I usually was accomplished within 2 to 3 days, differentiation in medium II took 4 to 5 days depending on the v-relER clone used. The differentiated cells survived in culture for additional 3 to 4 days.

Taken together, we demonstrate that clonal populations of v-relER cells can be efficiently induced to differentiate into two different cell types depending on the culture conditions employed. A low proportion of undifferentiated cells was retained, indicating that the culture conditions used might still be suboptimal for terminal differentiation of either cell type.

Characterization of dendritic v-relER cells

To characterize the differentiated v-relER cells obtained, several parameters were investigated. First, cellular ultrastructure was studied by electron microscopy. Second, the expression pattern of a panel of cell type-specific and lineage-specific markers was investigated. Third, the biological activity of the differentiated cells was assessed in functional assays.

The elongated, bipolar v-relER cells obtained in medium I were characterized by electron microscopy (FIG. 3). As can be seen, all organelles, vacuoles and other intracellular compartments localize to one side of the cell body (arbitrarily referred to as the basal side), while the opposite side contains a largely homogeneous cytoplasm with characteristic branching protrusions. Electron microscopy also revealed extended intermediate filament bundles on the basal side of the cell which were absent on the other side. These filament bundles may be important for the establishment and/or maintenance of the bipolar cell structure (see below). These morphological features provided the first hint that medium I-differentiated v-relER cells might represent avian dendritic cells.

While dendritic cells have been best characterized in mammals, their origin and identity is still poorly understood (reviewed in Steinman, 1991).

They represent professional antigen-presenting cells, characterized by their dendrite-like cytoplasmic protrusions, high expression of MHC class II antigens, moderate phagocytic activity and by their low capacity to adhere to tissue culture plastic.

Figure 4A:
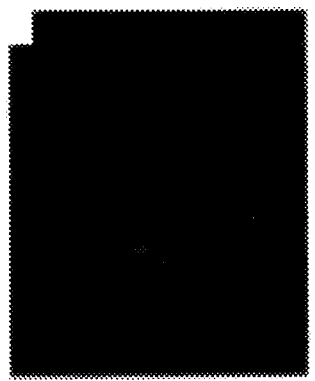
FIG. 4: Vimentin expression in dendritic and neutrophil v-relER cells. V-relER cells were induced to differentiate in medium I or medium II to generate dendritic cells (A, B, C) or neutrophils (D, E, F), respectively. The cells were allowed to adhere to adhesion slides and were subsequently subjected to indirect immunofluorescence employing a monoclonal anti-vimentin antibody. Following incubation with a FITC-labeled goat anti-mouse IgG, cells were mounted in antifade solution containing DAPI. The nuclear (A, D) and vimentin (B, E) staining were visualized by fluorescence microscopy involving a cooled charged coupled (CCD) camera and respective computer software, which allows to superimpose individual records (C, F). Please note that vimentin expression endows dendritic v-relER cells with a characteristic polarized appearance (C). The results shown here are obtained from clone 25 but were identical for other v-relER clones tested.
Figure 4B:
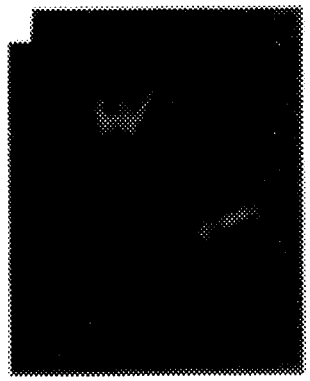
Figure 4C:
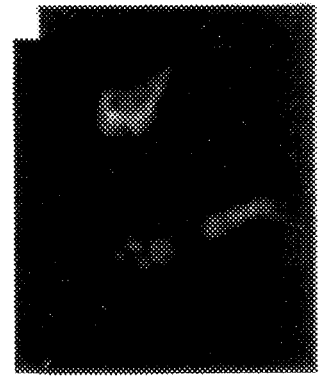
Figure 4D:
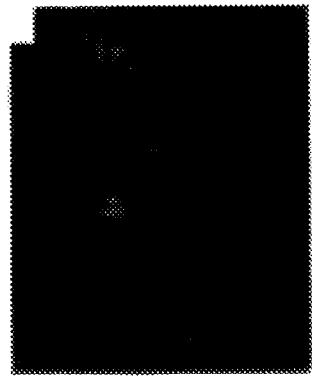
Figure 4E:
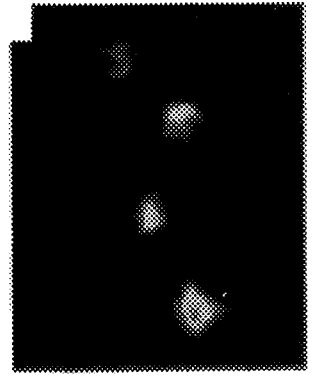
Figure 4F:
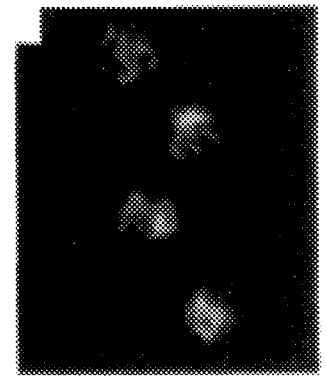

Previous work demonstrated that human skin dendritic (Langerhans) cells and dendritic cells from chicken bursa contain bundles of vimentin-type intermediate filaments (Mahrhe et al., 1983; DeWaal et al., 1984; Rappersberger et at., 1990; Olah and Glick, 1992; Olah et at., 1992a, 1992b). Because the electron micrographs in FIG. 3E, F clearly show bundles of intermediate filaments in longitudinal sections of dendritic v-relER cells, we analysed these cells for vimentin expression using indirect immunofluorescence. FIG. 4A shows that dendritic v-relER cells express vimentin in a characteristic polarized fashion, very similar to vimentin organization in dendritic cells of chicken bursa (Olah et al., 1992a, 1992b). Moreover, the polarized expression pattern appears to be characteristic for the dendritic cell type, since it was not detected for a number of other hematopoietic and nonhematopoietic cell types (data not shown). Rather, vimentin formed a "cage"-like structure surrounding the nucleus, as alto observed for v-rel transformed cells or undifferentiated v-relER cells (grown in the presence of estrogen). This "cage"-like structure was found to be reduced to a small vimentin aggregate in v-relER cells differentiated in medium II (FIGS. 4E, F).

Since dendritic cells are involved in MHC class II-dependent presentation of antigens to resting T helper cells (Steinman, 1991, and references therein), we next investigated MHC class II expression on differentiated dendritic v-relER cells. Cells were stained with a monoclonal antibody specific for the nonpolymorph region of the chicken B-L (MHC class II) β-chain and subjected to FACS analysis. All v-relER cell clones tested express high levels of MHC class II which is, however, independent of their differentiation state. (Table 1; see below FIG. 8A). High MHC class II expression in undifferentiated cells containing an active v-rel or v-relER oncoprotein could be due to transcriptional activation of the respective promoter which harbors clustered rel/NF-κB consensus sites (Zoorob et al., 1990).

Finally, a monoclonal antibody raised against dendritic cells of chicken spleen (CVI-ChNL-74.3; Jeurissen et al., 1992) revealed a spotted cytoplasmic staining pattern confined to the basal side of dendritic v-relER cells. A similar staining pattern was found in bona fide dendritic cells in chicken bursa. Staining in undifferentiated v-relER cells was perinuclear and weaker. In addition, the antibody also stained other hematopoietic cell types, albeit less efficiently (data not shown).

In summary, these results support the notion that the differentiated cells obtained from v-relER transformed chicken bone marrow cells exhibit properties of dendritic cells.

Assessment of functional properties of dendritic v-relER cells

To assess functional properties of differentiated v-relER cells, three assays were used: First, the phagocytic activity of v-relER cells was measured in order to discriminate dendritic cells (low activity) from macrophages (high activity). Second, since dendritic cells are very potent antigen-presenting cells, their ability to stimulate T cell proliferation in a primary mixed lymphocyte reaction (MLR) was assessed. Third, since dendritic cells are highly mobile, the behavior of individual v-relER transformed cells in culture was followed by time-lapse cinemicroscopy and video recording.

To measure phagocytic activity both, differentiated and undifferentiated v-relER cells were investigated for uptake of TRITC-labelled latex beads (diameter 0.48 μm). Several control cells were also tested, including normal bone marrow macrophages (which should exhibit high levels of phagocytic activity), T cells and erythroid cells which should have little or no activity.

Under the experimental conditions used, up to 20% of dendritic v-relER cells endocytosed 1–5 beads/cell within one hour (Table 2). Similar results were obtained for undifferentiated v-relER cells and v-rel transformed cells. These results are in accord with the early work of Lewis, et al. (1981) where the phagocytic activity of REV-T/REV-A transformed v-rel cells was measured. Bone marrow macrophages took up significantly more beads in the same period of time (85% of the cells contained 10–20 beads/cell), while T cells and erythroid cells were negative. Thus, dendritic v-relER cells exhibit a moderate phagocytic activity, as reported for normal dendritic cells (Steinman, 1991).

As an additional property to distinguish dendritic cells from macrophages, acid phosphatase activity was determined. Dendritic v-relER cells were consistently found to be negative, while control macrophages were highly positive (data not shown). This finding is in line with recent studies on dendritic cells in mammals (Zucker-Franklin et al., 1988).

Figure 5:
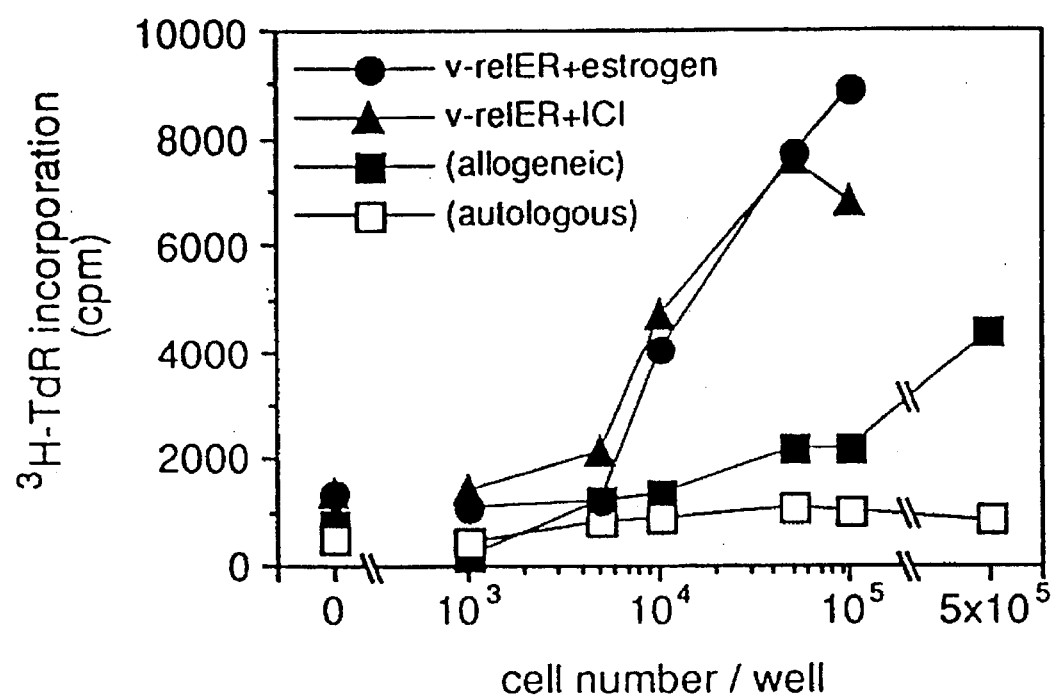
FIG. 5: V-relER cells stimulate primary T-lymphocytes in a mixed lymphocyte reaction (MLR). $2.5 \times 10^5$ primary spleen derived T-lymphocytes (of Lohmann Brown chick) were incubated for 5 days with $10^3$, $5 \times 10^3$, $10^4$, $5 \times 10^4$ and $10^5$ mitomycin C-treated v-relER cells. A proliferative response of stimulated T cells was determined by $^3$H-thymidine incorporation. Mitomycin C-treated autologous (Lohmann Brown) spleen cells induced no response, whereas spleen cells derived from the same chicken flock as v-relER cells (allogeneic, White Leghorn) induced a proliferative response only at high cell doses ($5 \times 10^5$ cells). For v-relER cells, estrogen or ICI was added to the MLR at day 1 of the experiment to keep the v-relER protein in the active or inactive state, respectively. Neither estrogen nor ICI had an effect on responder cells.

Among the antigen-presenting cells, dendritic cells are by far the most potent in inducing T cell responses (Steinman, 1991 and references therein). Therefore, undifferentiated and differentiated dendritic v-relER cells were investigated for their ability to stimulate proliferation of spleen T cells in primary dose-response MLR assays. FIG. 5 shows that dendritic v-relER cells are potent inducers of allogeneic T cell proliferation. $10 \times 10^3$ mitomycin C-treated dendritic v-relER cells were as efficient as $500 \times 10^3$ spleen cells, derived from the same chicken flock used to generate the v-relER cells. Maximal stimulation was obtained using $50 \times 10^3$ dendritic v-relER cells. As expected, autologous spleen cells failed to stimulate $^3$H-thymidine incorporation of responder T cells.

Surprisingly, undifferentiated v-relER cells (grown in the presence of estrogen) stimulated $^3$H-thymidine incorporation as efficiently as dendritic v-relER cells (FIG. 5). Whether this is a consequence of cytokine and/or growth factor production induced by the hormone-activated v-relER rather than an MLR remains to be shown. Production of differentiation and growth factor activities by v-rel transformed cells was demonstrated (Zenke et al., 1988; G. B. and P. Bartunek, data not shown). We also note that undifferentiated v-relER cells express high levels of MHC class II which is required for antigen presentation.

Figure 6A:
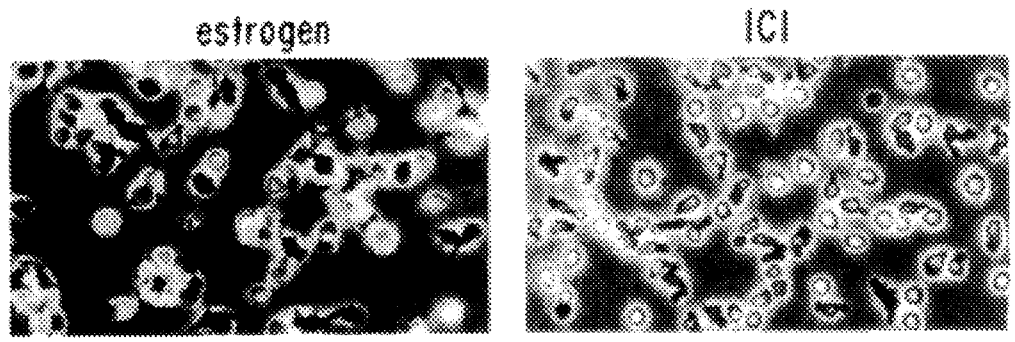
FIG. 6: Time-lapse cinemicroscopy of adherent v-relER cells. (A) V-relER cells adhere to tissue culture dishes, if grown in CEF-conditioned medium (CCE-medium), irrespective of the presence of estrogen or ICI. In the presence of estrogen spindle shaped cells with long dendritic processes are observed shortly after adherence (4–24 hours). In the presence of ICI cells stably (4–120 hours) acquire the elongated morphology usually observed for cells grown in suspension in medium I. Shown are cells cultured for 18 hours in CCE-medium.

One of the most striking features of dendritic cells is that they constantly generate, bend and retract cell processes which assume various shapes like spiny dendrites, bulbous pseudopods, and large thin cytoplasmic sheets or veils (reviewed by Zucker-Franklin et at., 1988; Steinman, 1991). To assess this property, we first established conditions where dendritic v-relER cells effectively adhered to the surface of the culture dish. Conditioned medium from chicken embryo fibroblasts (CCE-medium; see Experimental Procedures) was found to be most potent. While medium I-differentiated v-relER cells are nonadherent, incubation in CCE-medium plus ICI caused cells to effectively adhere to the culture dish within hours (FIG. 6A). However, in contrast to tightly adherent macrophages, dendritic v-relER cells could easily be dislodged by pipetting or brief EDTA treatment. Most importantly, adherent dendritic v-relER were found to be highly mobile, constantly forming large lamellipodia or veils.

Figure 6B:
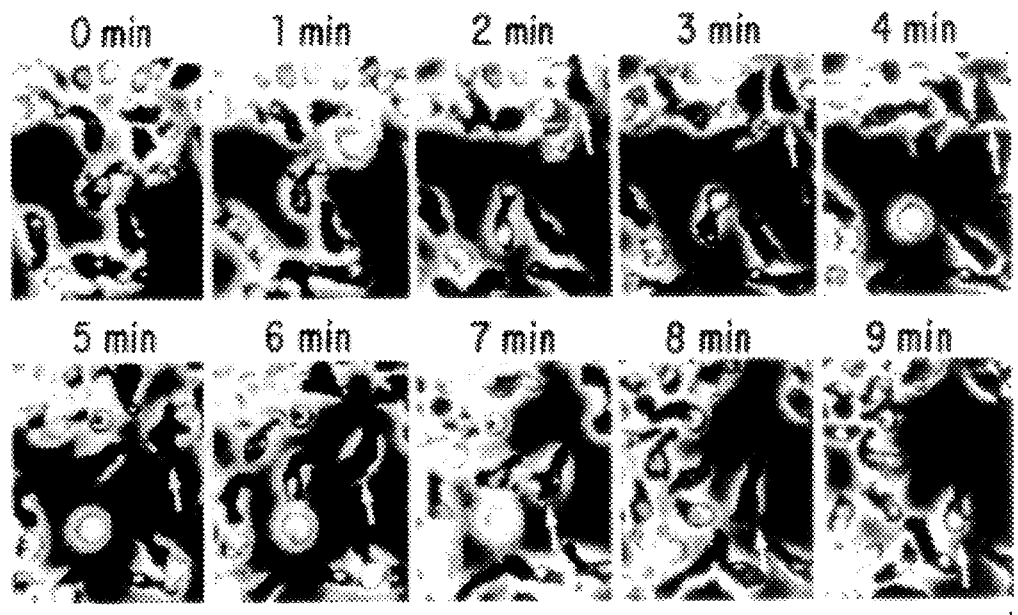

To follow the behavior of individual cells over an extended period of time, time-lapse cinemicroscopy and video recording was used. As shown in FIG. 6B, cells exhibiting the elongated, bipolar morphology continually contracted to form rounded cells, which then showed sheet-like processes (veils) and acquired again the elongated, bipolar phenotype. This process takes about 5–10 minutes, while cells move an average of 3–4 times their body length. The movement was, however, not directed (at least under the culture conditions employed so far). Additionally, no cell divisions were observed during the experimental period.

Undifferentiated v-relER cells incubated in CCE-medium (plus estrogen) also adhered to the surface of the culture dish (FIG. 6A). However, cells were still actively dividing, retained their round morphology and were by far less motile as compared to the dendritic v-relER cells described above. A minor cell population formed long spiny dendrite-like processes (FIG. 6A) but was still fully competent in undergoing cell divisions. v-rel transformed cells behaved identically (unpublished). This observation suggests that formation of long dendrite-like protrusions in v-relER and v-rel cells, requires both a component present in CCE-medium and some auxiliary rel or rel-equivalent activity. In addition, such cells were by far not as motile as the "veiled" v-relER cells obtained upon ICI-treatment in CCE-medium (see above). Whether this cell population represents more resident dendritic cells as opposed to the motile "veiled" dendritic cells, is not clear at present. We note, however, that these cells were devoid of acid phosphatase activity, thereby excluding that they represent macrophages (data not shown).

An important question is of course whether reactivation of v-relER affects cell mobility. Time-lapse cinemicroscopy revealed that administration of estrogen to "veiled" dendritic v-relER cells (obtained by ICI treatment in CCE-medium, see above) caused a dramatic reduction in their motility within 24–48 hours (data not shown). Control v-relER cells which were continuously kept in the presence of ICI retained their motility.

Figure 6C:
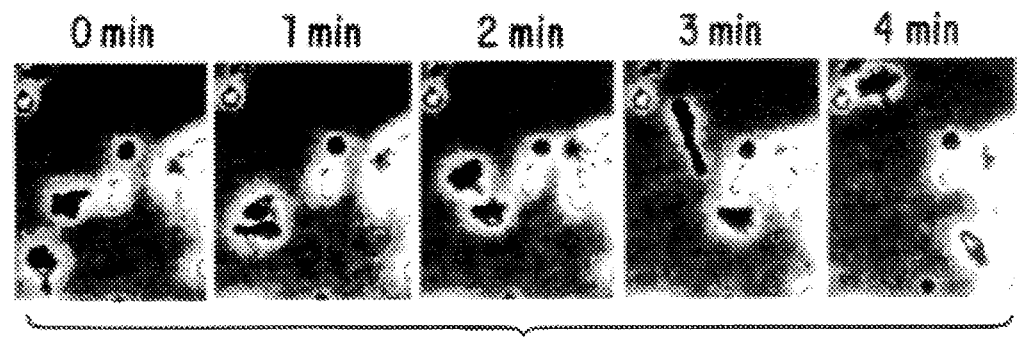

In conclusion, the high motility observed for "veiled" dendritic v-relER cells is very specific for this cell type and was not seen for other hematopoietic and non-hematopoietic cells (data not shown), suggesting that it reflects normal behavior of functional dendritic cells. This idea is strengthened by our finding that chicken spleen cell preparations enriched for dendritic cells, contained "veiled" cells which exhibited the same motility and characteristic way of moving as "veiled" dendritic v-relER cells (FIG. 6C).

Table 2: v-relER cells exhibit moderate phagoytic activity. Cells were incubated for 1 hour with TRITC-labeled latex beads in the respective growth medium. Following fixation, cells were mounted in antifade solution containing DAPI and analysed under fluorescence-illumination. The amount of intact cells containing phagocytosed fluorescent particles was evaluated by counting fields of 200–700 cells. The average percentage of positive cells from three independent experiments is shown with the respective standard deviations in brackets. Macrophages were the adherent cell fraction of a bone marrow culture, which also contained nonphagocytic stroma cells. With the exception of macrophages, all cell types shown contained 2–5 beads/cell. * indicates 10–20 beads/cell. The source for normal erythroblasts was a bone marrow mass culture treated for 20 days with TGFα and estrogen to selectively promote outgrowth of erythroid cells (Schroeder et at., 1993). Such cultures might contain a low percentage of persisting myeloid cells.

| cell type | % positive cells |
| --- | --- |
| v-relER | 19.3 (5.1) |
| dendritic v-relER | 12.7 (4.1) |
| v-rel | 11.0 (3.3) |
| erythroblasts | 1.2 (0.6) |
| macrophages | *85.1 (3.5) |

Generation of differentiated cells which exhibit the properties of neutrophilic granulocytes from v-relER cells As shown in FIGS. 1, 3 and 4, v-relER cells induced to differentiate in growth medium II exhibit a segmented polymorph nucleus. Such cells are also found in chicken bone marrow and peripheral chicken blood enriched for leukocytes by Ficoll-purification (FIG. 7C and data not shown) and resemble a cell type in birds referred to as heterophils (Lucas and Jamroz, 1961). Interestingly, during v-relER cell differentiation in medium II several intermediate nuclear forms were observed (FIG. 7A), reminiscent to a distinct pattern of nuclear maturation associated with neutrophil differentiation in humans (Zucker-Franklin et al., 1988). The round nucleus (stage 1) present in undifferentiated v-relER cells becomes "horseshoe-like" (stage 2), more and more indented (stage 3) and finally multilobed (stage 4). This process takes about 5 days and finally converts up to 75% of the cell population into polymorphonuclear cells (stage 3 and 4, FIG. 7B). As during differentiation of human neutrophils, a progressive loss of euchromatin and an increase of heterochromatin was observed (see FIG. 3).

Figure 7A:
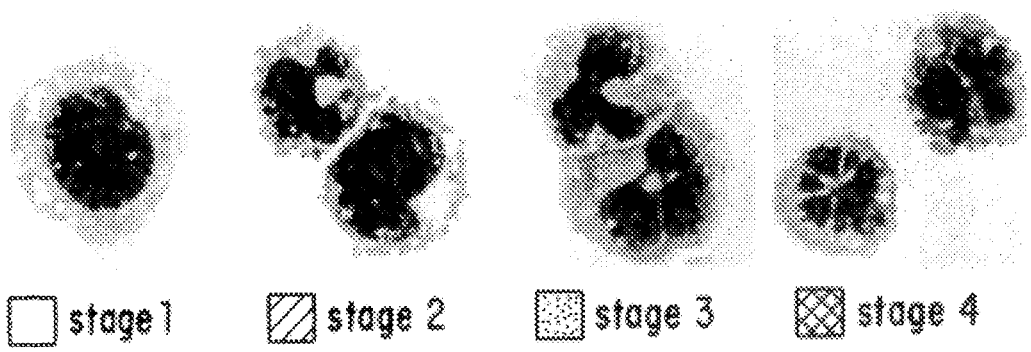
Figure 7C:
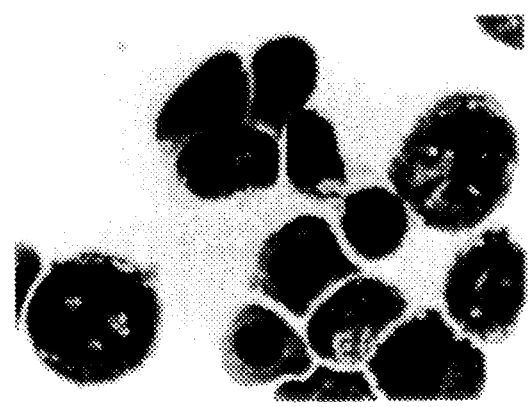
Figure 7D:
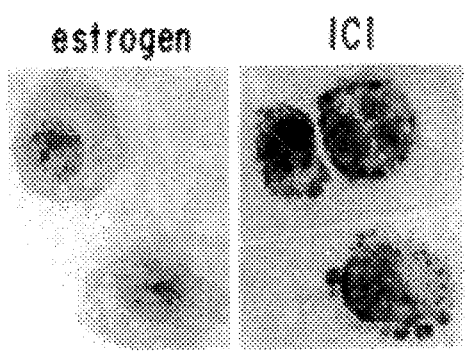
Figure 7B:
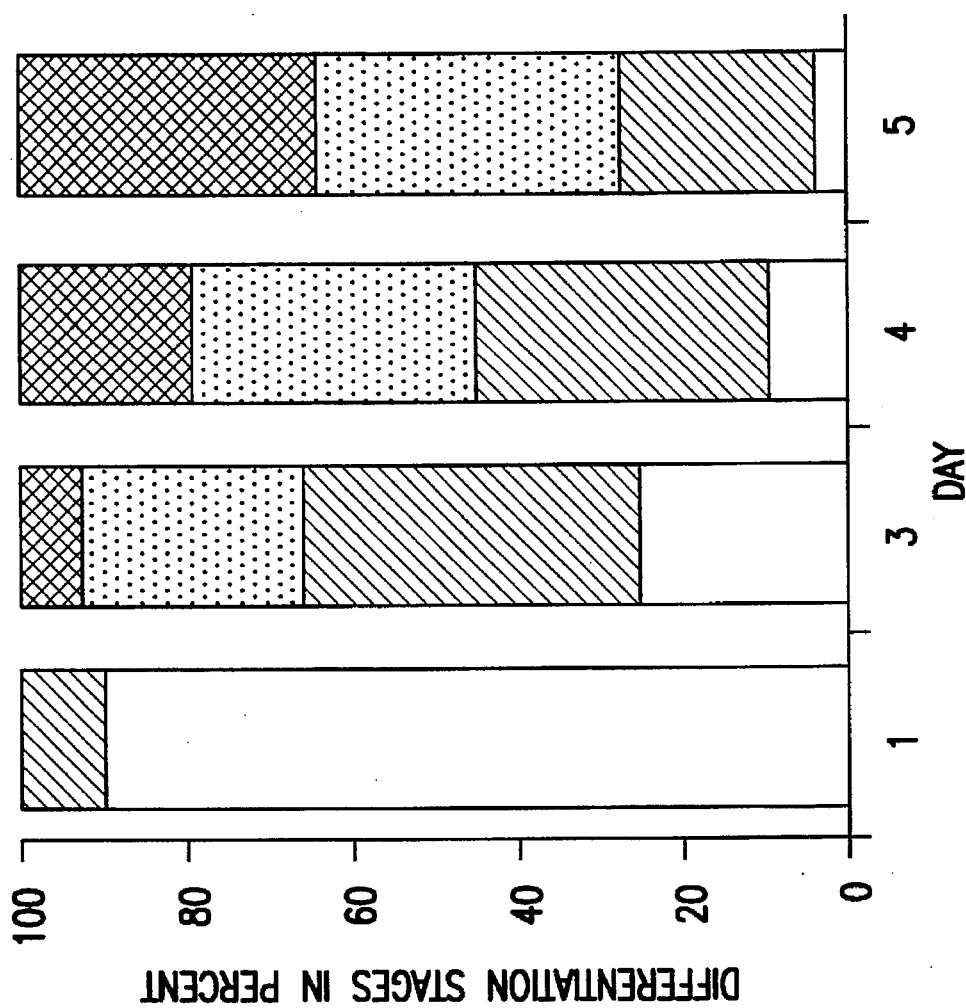

While mammalian neutrophils can readily be identified by established histological staining techniques (e.g., periodic acid-Schiff [PAS] reagent, Sudan Black staining; Zucker-Franklin et al., 1988), employing such stains for characterization of chicken neutrophils was less revealing. Yet PAS reagent (which detects glycogen, a major energy source of neutrophils) clearly stained medium II-differentiated v-relER cells. The staining pattern was, however, coarse (FIG. 7D) and apparently atypical as compared to that observed for normal human peripheral blood neutrophils (Zucker-Franklin et al., 1988). Undifferentiated and dendritic v-relER cells were PAS negative (FIG. 7D and data not shown). Detection of other neutrophil-specific markers (e.g., lactoferrin) has so far been met with only limited success. Most importantly, granules were not observed in medium II-differentiated v-relER cells, neither by employing various methods of histological staining nor by electron microscopy (FIGS. 1 and 3).

To get some further insight into the nature of medium II-differentiated v-relER cells, cells were analysed for min-1 protein expression employing Western blotting and a min-1-specific antibody. Min-1, distantly related to mammalian defensins, is expressed in normal and transformed promyelocytes and presumably also in normal neutrophils (Ness et al., 1989; Introna et al., 1990; Graf, 1992). We found that neither v-rel or v-relER transformed cells nor medium I- or II-differentiated v-relER cells express min-1 (data not shown).

In summary, several morphological criteria support the idea that medium II-differentiated v-relER cells represent neutrophils.

Characterization of undifferentiated v-relER cells

In early studies v-rel REV-T/REV-A transformed spleen or bone marrow cells were classified as early pre-B or pre-B/pre-T lymphoid progenitors (Beug et al., 1981; Lewis et al., 1981), while subsequent experiments suggested that one of the target cells transformed by v-rel is an IgM-positive B cell (Barth and Humphries, 1988; Zhang et al., 1989, 1991). This finding led several investigators to use such cells as a model system for studying B-lymphoid differentiation (Benatar, et al., 1991, 1992 and references therein). For these reasons, we investigated v-relER cells for expression of B-lymphoid determinants such as surface IgM expression, organization of the immunoglobulin (Ig) genes and expression of the B cell-specific activator protein BSAP.

First, all v-relER clones analysed and grown in the presence of estrogen express surface IgM, as shown by FACS analysis with an IgM-specific monoclonal antibody (Chen et al., 1982; FIG. 8A). Treatment with the phorbolester PMA further increased surface IgM expression to levels as high as that measured for the chicken B cell line RP9. However, IgM expression in such cells was still 5-fold lower than in primary cells from chicken bursa (not shown). Most importantly, when v-relER cells were induced to differentiate into dendritic cells, expression of surface IgM was downmodulated. Surface IgM expression was also low in cells simultaneously treated with ICI and PMA (FIG. 8A). Interestingly, under such conditions cells differentiated neither into dendritic cells nor into neutrophils, but exhibited a blast-like morphology and a round nucleus (data not shown). A more detailed analysis of this cell type is subject of current investigation. Finally, MHC class II expression remained high and unaffected under all conditions tested (see above), while erythroblasts were, as expected, negative for both IgM and MHC class II expression.

Second, to investigate the status of the Ig genes, genomic DNA isolated from undifferentiated and differentiated v-relER cells was digested with diagnostic restriction enzymes and analysed by Southern blotting. A BamHI/SalI restriction fragment of genomic DNA encompassing the J- to C-segment of the chicken lambda light chain gene (FIG. 8B; Reynaud et al., 1985, 1987) was used as a probe. FIG. 8B clearly shows that undifferentiated v-relER cells have the lambda chain gene rearranged, since the probe detects, in addition to the 16 kb and 2.8 kb EcoRI fragments (specific for the unrearranged allele), a 14 kb EcoRI fragment which is specific for the rearranged allele. This 14 kb EcoRI fragment was also observed in cells of chicken bursa (FIG. 8B; Reynaud et al., 1985), but was absent in CEFs (not shown). As expected, light chain gene rearrangement is irreversible and was observed in both undifferentiated v-relER cells and differentiated v-relER cells, irrespective whether differentiation was induced in medium I or II (FIG. 8B).

Third, we investigated v-relER cells for expression of the B cell specific activator protein BSAP. BSAP, encoded by the Pax-5 gene, is a member of the paired box transcription factor family (Adams et al., 1992). In the hematopoietic system of mammals BSAP is expressed during early stages of B cell development, but not in terminally differentiated plasma cells.

To detect BSAP activity in v-relER cells, nuclear extracts were prepared and analysed by electrophoretic mobility shift assay (EMSA). An oligonucleotide containing a binding site for mammalian BSAP (Barberis et al., 1990; Adams et al., 1992) was used. First we demonstrated that chicken BSAP contained in nuclear extracts of bursa produced a specific band, migrating at an identical position as mammalian BSAP (FIG. 9A and data not shown). BSAP binding to this site was specifically competed with an excess of the same but unlabelled oligonucleotide, while a mutated BSAP binding site competed less efficiently (FIG. 9A lanes 2 and 3, respectively). A murine BSAP-specific antibody, directed against the DNA binding ("paired") domain, interfered with DNA binding (FIG. 9A, lane 4). Most importantly, nuclear extracts of undifferentiated v-relER cells produced a specific band shift which migrated at identical position as observed for mammalian and chicken BSAP (FIG. 9A, lane 7). Additionally, extracts of undifferentiated v-relER cells treated with phorbolester PMA showed an increase in this activity (FIG. 9A, lane 9), in line with an increase in IgM expression in these cells (see above). Dendritic v-relER cells, however, were devoid of BSAP activity (FIG. 9A, lane 6). Interestingly, PMA treatment did not restore BSAP activity in v-relER cells kept in the presence of ICI (FIG. 9, lane 8), in line with the low surface IgM expression observed for these cells (FIG. 8A). Finally, oligonucleotide competition experiments and incubation with the BSAP-specific antibody confirmed that the DNA:protein complex formed in undifferentiated v-relER cells behaved as expected for chicken and mammalian BSAP (FIG. 9A, lanes 11–12; and data not shown). As expected, CEFs, used as an experimental control, did not contain BSAP activity (FIG. 9A).

While these experiments demonstrate that BSAP is expressed in undifferentiated v-relER cells, they also show that BSAP activity in these cells is considerably lower (about 50 fold) than that detected in bursa cells. This result was confirmed by measuring BSAP-specific mRNA levels in v-relER cells and chicken bursa. Therefore, chicken BSAP cDNA was cloned (P. D. and M. Busslinger, unpublished) and used for RNAse protection assays. As shown in FIG. 9B, BSAP is efficiently expressed in chicken bursa, while no expression is found in myeloid, erythroid and T cells. As expected, undifferentiated v-relER cells express low amounts of BSAP-specific mRNA, which is augmented by PMA treatment (FIG. 9B). No BSAP mRNA was detected in differentiated v-relER cells, both with and without PMA treatment.

In summary, these experiments demonstrate that undifferentiated v-relER cells exhibit properties of B-lymphoid cells, which, however, are downmodulated or lost when dendritic cell differentiation is induced. As expected, the rearranged state of the Ig light chain gene is preserved in differentiated v-relER cells, indicating that Ig gene rearrangement does not interfere with their differentiation into neutrophils and dendritic cells.

It will be appreciated to those skilled in the art that the invention can be performed within a wide range of equivalent parameters of composition, concentrations, modes of administration, and conditions without departing from the spirit or scope of the invention or any embodiment thereof.

The disclosures of all publications, references, patent applications and patents recited herein are hereby incorporated by reference.

References

Adams, B., Dörfler, P., Aguzzi, A., Kozmik, Z., Urbánek, P., Maurer-Fogy, I. and Busslinger, M. (1992). Pax-5 encodes the transcription factor BSAP and is expressed in B lymphocytes, the developing CNS, and adult testis. *Genes Dev.* 6: 1589–1607.

Ballard, D. W., Walker, W. H., Doerre, S., Sista, P., Molitor, J. A., Dixon, E. P., Peffer, N. J., Hannink, M. and Greene, W. C. (1990). The v-rel oncogene encodes a kappa B enhancer binding protein that inhibits NF-kappa B function. *Cell* 63:803–814.

Ballard, D. W., Dixon, E. P., Peffer, N. J., Bogerd, H., Doerre, S., Stein, B. and Greene, W. C. (1992). The 65-kDa subunit of human NF-kappa B functions as a potent transcriptional activator and a target for v-Rel-mediated repression. *Proc. Natl. Acad. Sci. USA* 89:1875–1879.

Barberis, A., Widenhorn, K., Vitelli, L. and Busslinger, M. (1990). A novel B-cell lineage-specific transcription factor present at early but not late stages of differentiation. *Genes Dev.* 4:849–859.

Barka, T. and Anderson, P. J. (1962). Histochemical method for acid phosphatase using pararosaniline as coupler. *J. Histochem. Cytochem.* 10:741–753.

Barth, C. F. and Humphries, E. H. (1988). Expression of v-rel induces mature B-cell lines that reflect the diversity of avian immunoglobulin heavy-and light-chain rearrangements. *Mol. Cell. Biol.* 8:5358–5368.

Barth, C. F., Ewert, D. L., Olson, W. C. and Humphries, E. H. (1990). Reticuloendotheliosis virus REV-T(REV-A)-induced neoplasia: development of tumors within the T-lymphoid and myeloid lineages. *J. Virol.* 64:6054–6062.

Benatar, T., Iacampo, S., Tkalec, L. and Ratcliffe, M. J. (1991). Expression of immunoglobulin genes in the avian embryo bone marrow revealed by retroviral transformation. *Eur. J. Immunol.* 21:2529–2536.

Benatar, T., Tkalec, L. and Ratcliffe, M. J. (1992). Stochastic rearrangement of immunoglobulin variable-region genes in chicken B-cell development. *Proc. Natl. Acad. Sci. USA* 89:7615–7619.

Beug, H., von Kirchbach, A., Doederlein, G., Conscience, J. F. and Graf, T. (1979). Chicken hematopoietic cells transformed by seven strains of defective avian leukemia viruses display three distinct phenotypes of differentiation. *Cell.* 18:375–390.

Beug, H., Müller, H., Grieser, S., Doederlein, G. and Graf, T. (1981). Hematopoietic cells transformed in vitro by REV-T avian reticuloendotheliosis virus express characteristics of very immature lymphoid cells. *Virology* 115:295–309.

Beug, H. and Graf, T. (1989). Co-operation between viral oncogenes in avian erythroid and myeloid leukemia. *Eur. J. Clin. Invest.* 19:491–502.

Boehmelt, G., Walker, A., Kabrun, N., Mellitzer, G., Beug, H., Zenke, M. and Enrietto, P. J. (1992). Hormone-regulated v-rel estrogen receptor fusion protein: reversible induction of cell transformation and cellular gene expression. *EMBO J.* 11:4641–4652.

Bose, H. J. (1992). The Rel family: models for transcriptional regulation and oncogenic transformation. *Biochim. Biophys. Acta* 1114:1–17.

Bowler, J., Lilley, T. J., Pittam, J. T. and Wakeling, A. E. (1989). *Steroids* 54:71–99.

Burk and Klempnauer, *EMBO J.* 10:3713–3719 (1991).

Capobianco, A. J. and Gilmore, T. D. (1993). A conditional mutant of vRel containing sequences from the human estrogen receptor. *Virology* 193:160–170.

Caux, C., Dezutter, D.C., Schmitt, D. and Banchereau, J. (1992). GM-CSF and TNF-alpha cooperate in the generation of dendritic Langerhans cells. *Nature* 360:258–261.

Chen, C.-L., Lehmeyer, J. E. and Cooper, M. D. (1982). Evidence for an IgD homologue on chicken lymphocytes. *J. Immunol.* 129:2580–2585.

Dauvois, S., Danielian, D. S., White, R. and Parker, M. G. (1992). Antiestrogen ICI 164,384 reduces cellular estrogen receptor content by increasing its turnover. *Proc. Natl. Acad. Sci. USA* 89:4037–4041.

DeWaal, R. M. W., Semeiju, J. T., Cornelissen, I. M. H. and Ramaekers, F. C. (1984). Epidermal Langerhans cells contain intermediate-sized filaments of the vimentin type. An immunocytologic study. *J. Invest. Dermatol.* 82:602–604.

Eilers et al., *Nature* 340:66–68 (1989).

Fracchiolla, N. S., Lombardi, L., Salina, M., Migliazza, A., Baldini, L., Berti, E., Cro, L., Polli, E., Maiolo, A. T. and Neri, A. (1993). Structural alterations of the NF-kappa B transcription factor lyt-10 in lymphoid malignancies. *Oncogene* 8:2839–2845.

Gilmore, T. D. (1991). Malignant transformation by mutant Rel proteins. *Trends Genet* 7:318–322.

Graf, T. (1992). Myb: a transcriptional activator linking proliferation and differentiation in hematopoietic cells. *Curr. Opin. Genet. Dev.* 2:249–255.

Greaves, M. F., Chan, L. C., Furley, A. J., Watt, S. M. and Molgaard, H. V. (1986). Lineage promiscuity in hemopoietic differentiation and leukemia. *Blood* 67:1–11.

Heinen, E. and Bosseloir, A. (1994). Follicular dendritic cells: whose children? *Immunology Today* 15:201–204.

Hughes, S. H., Greenhouse, J. J., Petropoulos, C. J. and Sutrave, P. (1987). *J. Virol.* 61:3004–3012.

Inaba, K., Inaba, M., Romani, N., Aya, H., Deguchi, M., Ikehara, S., Muramatsu, S. and Steinman, R. M. (1992). Generation of large numbers of dendritic cells from mouse bone marrow cultures supplemented with granulocyte/macrophage colony-stimulating factor. *J. Exp. Med.* 176:1693–1702.

Inaba, K., Inaba, M., Deguchi, M., Hagi, K., Yasumizu, R., Ikehara, S., Muramatsu, S. and Steinman, R. M. (1993). Granulocytes, macrophages, and dendritic cells arise from a common major histocompatibility complex class II-negative progenitor in mouse bone marrow. *Proc. Natl. Acad. Sci. USA* 90:3038–3042.

Inoue, J., Kerr, L. D., Ransone, L. J., Bengal, E., Hunter, T. and Verma, I. M. (1991). c-rel activates but v-rel suppresses transcription from kappa B sites. *Proc. Natl. Acad. Sci. USA* 88:3715–3719.

Introna, M., Golay, J., Frampton, J., Nakano, T., Ness, S. A. and Graf, T. (1990). Mutations in v-myb alter the differentiation of myelomonocytic cells transformed by the oncogene. *Cell* 63:1289–1297.

Jackson, P., Baltimore, D. and Didier, P. (1993). Hormone-conditional transformation by fusion proteins of c-Abl and its transforming variants. *EMBO Journal* 12(7):2809–2819.

Jeurissen, S. H., Claassen, E. and Janse, E. M. (1992). Histological and functional differentiation of non-lymphoid cells in the chicken spleen. *Immunology* 77:75–80.

Kaufman, J., Skjødt, K., Salomonsen, J., Simonsen, M., Du Pasquier, L., Parisot, R. and Riegert, P. (1990). MHC-like molecules in some nonmammalian vertebrates can be detected by some cross-reactive xenoantisera. *J. Immunol.* 144:2258–2272.

Kornfeld, S., Beug, H., Doederlein, G. and Graf, T. (1983). Detection of avian hematopoietic cell surface antigens with monoclonal antibodies to myeloid cells. Their distribution on normal and leukemic cells of various lineages. *Exp. Cell Res.* 143:383–394.

Kumar, V., Green, S., Staub, A. and Chambon, P. (1986) *EMBO J.* 5:2231–2236.

Lewis, R. B., McClure, J., Rup, B., Niesel, D. W., Garry, R. F., Hoelzer, J. D., Nazerian, K. and Bose, H. J. (1981). Avian reticuloendotheliosis virus: identification of the hematopoietic target cell for transformation. *Cell* 25:421–431.

Lu, D., Thompson, J. D., Gorski, G. K., Rice, N. R., Mayer, M. G. and Yunis, J. J. (1991). Alterations at the rel locus in human lymphoma. *Oncogene* 6:1235–1241.

Lucas, A. M. and Jamroz, C. (1961). Atlas of Arian Hematology, Agriculture Monograph 25, United States Department of Agriculture, Washington.

Mahrhe, G. R., Bolling, R., Osborn, M. and Weber, K. (1983). Intermediate filaments of the vimentin and prekeratin type in human epidermis. *J. Invest. Dermatol* 81:46–48.

Mattioni, T., Louvion, J. F. and Picard, D. (1994). Regulation of protein activities by fusion to steroid-binding domains. *Methods in Cell Biology* 43:335–352.

Meisenberg et al., *Blood* 79:2267 (1992).

McCulloch, E. A. (1983). Stem cells in normal and leukemic hemopoiesis. *Blood* 62:1–13.

McDonnell, P. C., Kumar, S., Rabson, A. B. and Gelinas, C. (1992). Transcriptional activity of rel family proteins. *Oncogene* 7:163–170.

Morrison, L. E., Kabrun, N., Mudri, S., Hayman, M. J. and Enrietto, P. J. (1989). Viral rel and cellular rel associate with cellular proteins in transformed and normal cells. *Oncogene* 4:677–683.

Morrison, L. E., Boehmelt, G., Beug, H. and Enrietto, P. J. (1991). Expression of v-rel in a replication competent virus: transformation and biochemical characterization. *Oncogene* 6:1657–1666.

Morrison, L. E., Boehmelt, G. and Enrietto, P. J. (1992). Mutations in the rel-homology domain alter the biochemical properties of v-rel and render it transformation defective in chicken embryo fibroblasts. *Oncogene* 7:1137–1147.

Narayanan et al., *Science* 256:367–370 (1992).

Neri, A., Chang, C. C. Lombardi, L., Salina, M., Corradini, P., Maiolo, A. T., Chaganti, R. S. and Dalla, F. R. (1991). B cell lymphoma-associated chromosomal translocation involves candidate oncogene lyt-10, homologous to NF-kappa B p50. *Cell* 67:1075–1087.

Ness, S. A., Marknell, A. and Graf, T. (1989). The v-myb oncogene product binds to and activates the promyelocyte-specific min-1 gene. *Cell* 59:1115–1125.

Olah, I. and Glick, B. (1992). Follicle-associated epithelium and medullary epithelial tissue of the bursa of fabricius are two different compartments. *Anat. Rec.* 233:577–587.

Olah, I., Kendall, C. and Glick, B. (1992a). Anti-vimentin monoclonal antibody recognizes a cell with dendritic appearance in the chicken's bursa of Fabricius. *Anat. Rec.* 232:121–125.

Olah, I., Kendall, C. and Glick, B. (1992b). Differentiation of bursal secretory-dendritic cells studied with anti-vimentin monoclonal antibody. *Anat. Rec.* 233:111–120.

Olson, L. D. (1967). Histopathologic and hematologic changes in moribund stages of chicks infected with T-virus. *Am. J. Vet. Res.* 28:1501–1507.

Olson, W. C. and Ewert, D. L. (1990). Markers of B lymphocyte differentiation in the chicken. *Hybridoma* 9:331–350.

Paglia, P., Girolomoni, G., Robbiati, F., Granucci, F. and Ricciardi-Castagnoli, P. (1993). Immortalized dendritic cell line fully competent in antigen presentation initiates primary T cell responses in vivo. *J. Exp. Med.* 178:1893–1901.

Picard et al., *Cell* 54:1073–1080 (1988).

Radke, K., Beug, H., Kornfeld, S. and Graf, T. (1982). Transformation of both erythroid and myeloid cells by E26, an avian leukemia virus that contains the myb gene. *Cell* 31:643–653.

Rappersberger, K., Binder, M., Zonzits, E., Hornick, U. and Wolff, K. (1990). Immunogold staining of intermediate sized filaments of the vimentin type in human skin: A postembedding immunoelectron microscopic study. *J. Invest. Dermatol.* 94:700–705.

Reynaud, C. A., Anquez, V., Dahan, A. and Weill, J. C. (1985). A single rearrangement event generates most of the chicken immunoglobulin light chain diversity. *Cell* 40:283–291.

Reynaud, C. A., Anquez, V., Grimal, H. and Weill, J. C. (1987). A hyperconversion mechanism generates the chicken light chain preimmune repertoire. *Cell* 48:379–388.

Reynaud, C. A., Imhof, B. A., Anquez, V. and Weill, J. C. (1992). Emergence of committed B lymphoid progenitors in the developing chicken embryo. *EMBO J.* 11:4349–4358.

Richardson, P.M. and Gilmore, T. D. (1991). vRel is an inactive member of the Rel family of transcriptional activating proteins. *J. Virol.* 65:3122–3130.

Romani, N., Gruner, S., Brang, D., Kämpgen, E., Lenz, A., Trockenbacher, B., Konwalinka, G., Fritsch, P. O., Steinmann, R. M. and Schuler, G. (1994). Proliferating dendritic cell progenitors in human blood. *J. Exp. Med.* 180:83–93.

Sallusto, F. and Lanzavecchia, A. (1994). Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor a. *J. Exp. Med.* 179:1109–1118.

Scherrer, L. C., Picard, D., Massa, E., Harmon, J. M., Simons, Jr., S. S., Yamamoto, K. R. and Pratt, W. B. (1993). Evidence that the Hormone Binding Domain of Steroid Receptors Confers Hormonal Control of Chimeric Proteins by Determining Their Hormone-Regulated Binding to Heat-Shock Protein 90. *Biochemistry* 32:5381–5386.

Schreiber, E., Matthias, P., Müller, M. M. and Schaffner, W. (1989). Rapid detection of octamer binding proteins with 'mini-extracts', prepared from a small number of cells. *Nuc. Acids Res.* 17:6419.

Schroeder, C., Gibson, L., Nordstrom, C. and Beug, H. (1993). The estrogen receptor cooperates with the TGF alpha receptor (c-erbB) in regulation of chicken erythroid progenitor self-renewal. *EMBO J.* 12:951–960.

Sevoian, M., Larose, R. N. and Chamberlain, D. M. (1964). Avian Lymphomatosis. VI. A virus of unusual potency and pathogenicity. *Avian Dis.* 8:336–347.

Sheehan, H. L. and Storey, G. W. (1947). An improved method of staining leukocyte granules with Sudan Black B. *J. Pathol. Bacteriol.* 59:336.

Steinman, R. M., Kaplan, G., Witmer, M. D. and Cohn, Z. A. (1979). Identification of a novel cell type in peripheral lymphoid organs of mice. Purification of spleen dendritic cells, new surface markers, and maintenance in vitro. *J. Exp. Med.* 149:1–16.

Steinman, R. M. (1991). The dendritic cell system and its role in immunogenicity. *Annu. Rev. Immunol.* 9:271–296.

Superti-Furga et at., *Proc. Natl. Acad. Sci. USA* 88:5114–5118 (1991).

Theilen, G. H., Zeigel, R. F. and Twiehaus, M. J. (1966). Biological studies with RE virus (strain T) that induces reticuloendotheliosis in turkeys, chickens, and Japanese quail. *J. Natl. Cancer Inst.* 37:731–743. Umek et al., *Science* 251:288–292 (1991).

Umek, R. M., Friedman, A.D. and McKnight, S. L. (1991). CCAAT-enhancer binding protein: A component of a differentiation switch. *Science* 251:288–292.

Vitelli, L., Kemler, I., Lauber, B., Birnstiel, M. L. and Busslinger, M. (1988). Developmental Regulation of Micro-Injected Histone Genes in Sea Urchin Embryos. *Developmental Bid.* 127:54–63.

Wakeling, A. E. and Bowler, J. (1988). *J. Steroid Biochem.* 30:141–148.

White, D. W. and Gilmore, T. D. (1993). Temperature-sensitive transforming mutants of the v-rel oncogene. *J. Virol.* 67:6876–6881.

Zenke, M., Kahn, P., Disela, C., Vennstrom, B., Leutz, A., Keegan, K., Hayman, M., Choi. H. R., Yew, N., Engel, D., and Beug, H. (1988). v-erbA specifically suppresses transcription of the avian erythrocyte anion transporter (band 3) gene. *Cell* 52:107–119.

Zhang, J. Y., Bargmann, W. and Bose, H. J. (1989). Rearrangement and diversification of immunoglobulin light-chain genes in lymphoid cells transformed by reticuloendotheliosis virus. *Mol. Cell Biol.* 9:4970–4976.

Zhang, J. Y., Olson, W., Ewert, D., Bargmann, W. and Bose, H. J. (1991). The v-rel oncogene of avian reticuloendotheliosis virus transforms immature and mature lymphoid cells of the B cell lineage in vitro. *Virology* 183:457–466.

Zoorob, R., Béhar, G., Kroemer, G. and Auffray, C. (1990). Organization of a functional chicken class II B gene. *Immunogenetics* 31:179–187.

Zucker-Franklin, D., Greaves, M. F., Grossi, C. E. and Marmont, A. M. (1988). Atlas of Blood Cells, Function and Pathology 1, Gustav Fischer Stuttgart, Germany, 157–377.

---

---

What is claimed is:

1. A method for inducing differentiation of transformed hematopoietic cells during culture, the method comprising:
    (a) introducing into the hematopoietic cells an oncogene which expresses an oncoprotein, wherein said oncoprotein transforms immature hematopoietic cells;
    (b) culturing the cells in a first culture medium under conditions wherein said oncogene expresses said oncoprotein which promotes cellular growth while at least partially inhibiting cellular differentiation;
    (c) deactivating said oncoprotein or expression from said oncogene to induce cellular differentiation; and
    (d) culturing the cells in a second culture medium which induces the differentiation of hematopoietic cells.

2. The method of claim 1, wherein said differentiated cells have the morphological and functional characteristics of dendritic cells.

3. The method of claim 1, wherein said differentiated cells have the morphological and functional characteristics of polymorphonuclear neutrophils.

4. The method of claim 1, wherein said oncogene encodes a temperature sensitive mutant oncoprotein.

5. The method of claim 4, wherein, in step (b), the conditions wherein said temperature sensitive mutant oncoprotein promotes cellular growth while at least partially inhibiting cellular differentiation comprise culturing at a permissive temperature.

6. The method of claim 5, wherein, in step (c), said temperature sensitive mutant oncoprotein is deactivated by culturing at a non-permissive temperature.

7. The method of claim 4, wherein said oncogene encodes a temperature sensitive transcription factor selected from the Rel family of proteins.

8. The method of claim 7, wherein said oncogene encodes a temperature sensitive v-rel mutant.

9. The method of claim 1, wherein said oncogene encodes a hormone-dependent fusion protein comprising all or part of an oncoprotein fused to all or part of a hormone receptor.

10. The method of claim 9, wherein, in step (b), the conditions wherein said oncoprotein promotes cellular growth while at least partially inhibiting cellular differentiation comprise culturing in the presence of a hormone or hormone agonist specific for said hormone receptor.

11. The method of claim 10, wherein, in step (c), said hormone-dependent fusion protein is deactivated by removing said hormone or hormone agonist.

12. The method of claim 10, wherein, in step (c), said hormone-dependent fusion protein is deactivated by culturing in the presence of a hormone antagonist.

13. The method of claim 9, wherein said hormone-dependent fusion protein comprises all or part of a transcription factor oncoprotein selected from the Rel family of proteins.

14. The method of claim 13, wherein said oncoprotein is all or part of v-rel.

15. The method of claim 10, wherein said hormone is estrogen.

16. The method of claim 10, wherein said agonist is OHT.

17. The method of claim 12, wherein said antagonist is ICI 164,384.

18. The method of claim 2, wherein in step (d), said second culture medium contains transferrin and insulin.

19. The method of claim 18, wherein said second medium further contains fibroblast conditioned medium.

20. The method of claim 3, wherein in step (d), said second culture medium is selected from CFU-E medium or modified CFU-E medium.

21. The method of claim 1, wherein said hematopoietic cells are isolated from a source selected from bone marrow, peripheral blood, or umbilical cord blood.

22. The method of claim 21, wherein said cells are isolated from bone marrow.

23. The method of claim 1, wherein said hematopoietic cells are from a vertebrate.

24. The method of claim 23, wherein said cells are avian.

25. The method of claim 24, wherein said avian cells are chicken.

26. The method of claim 1, wherein in step (a), said oncogene is introduced into the hematopoietic cells by viral infection.

27. The method of claim 1, wherein in step (c), said oncoprotein or expression from said oncogene is deactivated during culture in said first culture medium.

28. The method of claim 1, wherein in step (c), said oncoprotein or expression from said oncogene is deactivated after culture in said first culture medium.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GCGGAATTCA GRTA Y TA Y GA RACNG-
GNAG Y AT                                    3 2
```

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GCGGTCGACR AT Y TCCCANG CRAACATNGT NGG                              33
```

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
CAGGGTTGTG ACGCAGCGGT GGGTGACGAC TGTCGG                             36
```

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CAGGGTTGTG ACGAAGCGGT GGGTGACGAC TGTCGG                             36
```